United States Patent [19]
Caro et al.

[11] Patent Number: 5,830,131
[45] Date of Patent: *Nov. 3, 1998

[54] APPARATUS AND METHOD FOR MEASURING AN INDUCED PERTURBATION TO DETERMINE A PHYSICAL CONDITION OF THE HUMAN ARTERIAL SYSTEM

[75] Inventors: Richard G. Caro; Mark H. Sher, both of San Francisco; Bryan P. Flaherty, Half Moon Bay, all of Calif.

[73] Assignee: Vital Insite, Inc., South San Francisco, Calif.

[*] Notice: The term of this patent shall not extend beyond the expiration date of Pat. No. 5,590,649.

[21] Appl. No.: 561,928

[22] Filed: Nov. 22, 1995

Related U.S. Application Data

[63] Continuation-in-part of Ser. No. 228,213, Apr. 15, 1994, Pat. No. 5,590,649.

[51] Int. Cl.$^6$ ....................................................... A61B 5/00
[52] U.S. Cl. ......................... 600/300; 600/485; 600/500; 600/504; 600/481; 600/479; 600/561; 600/587
[58] Field of Search ................................ 126/603, 633, 126/630, 664–8, 672–694, 696, 713, 716, 719, 721, 722, 735, 748, 774

[56] References Cited

U.S. PATENT DOCUMENTS

| | | | |
|---|---|---|---|
| 3,090,377 | 5/1963 | Salisbury et al. | 128/2.05 |
| 3,095,872 | 7/1963 | Tolles | 128/2.05 |
| 3,885,551 | 5/1975 | Massie . | |
| 4,646,754 | 3/1987 | Seale | 128/677 |
| 4,718,426 | 1/1988 | Russell . | |

(List continued on next page.)

FOREIGN PATENT DOCUMENTS

| | | |
|---|---|---|
| 0 443 267 A1 | 8/1991 | European Pat. Off. . |
| WO 86/04801 | 8/1986 | WIPO . |
| WO90/00029 | 1/1990 | WIPO . |
| WO 95/16391 | 6/1995 | WIPO . |

OTHER PUBLICATIONS

"Characteristics of Impact and Pulse Wave Propagation in Brachial and Radial Arteries", Milton Landowne, vol. 12, Jan. 1958, pp. 91–97.

(List continued on next page.)

*Primary Examiner*—Robert L. Nasser
*Attorney, Agent, or Firm*—Flehr Hohbach Test Albritton & Herbert LLP

[57] ABSTRACT

A monitor for determining a patient's physical condition includes a calibration device configured to provide a calibration signal representative of a patient's physiological parameter. An exciter is positioned over a blood vessel of the patient for inducing a transmitted exciter waveform into the patient. A noninvasive sensor is positioned over the blood vessel, where the noninvasive sensor is configured to sense a hemoparameter and to generate a noninvasive sensor signal representative of the hemoparameter containing a component of a physiological parameter waveform and a component of a received exciter waveform. In this context, a hemoparameter is defined as any physiological parameter related to vessel blood such as pressure, flow, volume, velocity, blood vessel wall motion, blood vessel wall position and other related parameters. A processor is configured to determine a relationship between a property of the received exciter waveform and a property of the physiological parameter. The processor is connected to receive the calibration signal and the noninvasive sensor signal, and the processor is configured to process the calibration signal and the noninvasive sensor signal to determine the physical condition. In an exemplary embodiment, the physical condition is arterial stiffness that represents cardiovascular disease, however, many additional physical conditions can be measured and determined such as arterial elasticity, arterial thickness, arterial wall compliance and other conditions. Also, in an exemplary embodiment, the physiological parameter measured is blood pressure, however, the present invention can also be used to analyze and track other physiological parameters

57 Claims, 16 Drawing Sheets

U.S. PATENT DOCUMENTS

| | | | |
|---|---|---|---|
| 4,771,792 | 9/1988 | Seale . | |
| 4,869,261 | 9/1989 | Penaz . | |
| 4,873,987 | 10/1989 | Djordjevich et al. . | |
| 5,111,817 | 5/1992 | Clark et al. .............................. | 128/633 |
| 5,148,807 | 9/1992 | Hsu . | |
| 5,241,963 | 9/1993 | Shankar .................................. | 128/694 |
| 5,241,964 | 9/1993 | McQuilkin .............................. | 128/672 |
| 5,267,565 | 12/1993 | Beard ...................................... | 128/687 |
| 5,279,303 | 1/1994 | Kawamura et al. ..................... | 128/683 |
| 5,533,511 | 7/1996 | Kaspari et al. .......................... | 128/672 |

OTHER PUBLICATIONS

"Dispersion and Attenuation of Small Artificial Pressure Waves in the Canine Aorta", Max Anliker, Ph.D., Michael B. Histand, M.S., and Eric Ogden, MRCS, LRCP, Circulation Research, vol. XXIII, Oct. 1968, pp. 539–551.

"Measurement of Pulse–Wave Velocity Using a Beat–Sampling Technique", J.D. Pruett, J.D. Bourland, L.A. Geddes, Annals of Biomedical Engineering, vol. 16, pp. 341–347, 1988.

"Application Note #3 About Lock–In Amplifiers", Stanford Research Systems, Scientific and Engineering Instruments, 1992–1993, pp. 129–139.

"Vibration technique for indirect measurement of diastolic arterial pressure in human fingers", H. Shimazu, H. Ito, A. Kawarada, H. Kobayashi, A. Hiraiwa, K. Yamakoshi, Med. & Biol. Eng. & Comput., Mar. 1989, 27, pp. 130–136.

"Continuous Non–Invasive Blood Pressure Measurement Using Arterial Pressure Wave Velocity", R.G. Pearl, L.C. Siegel, T. Nishimura, M.H. Sher, B.T. Flaherty, J. McLoughlin, R.C. Caro, STanford University School of Medicine, 1995.

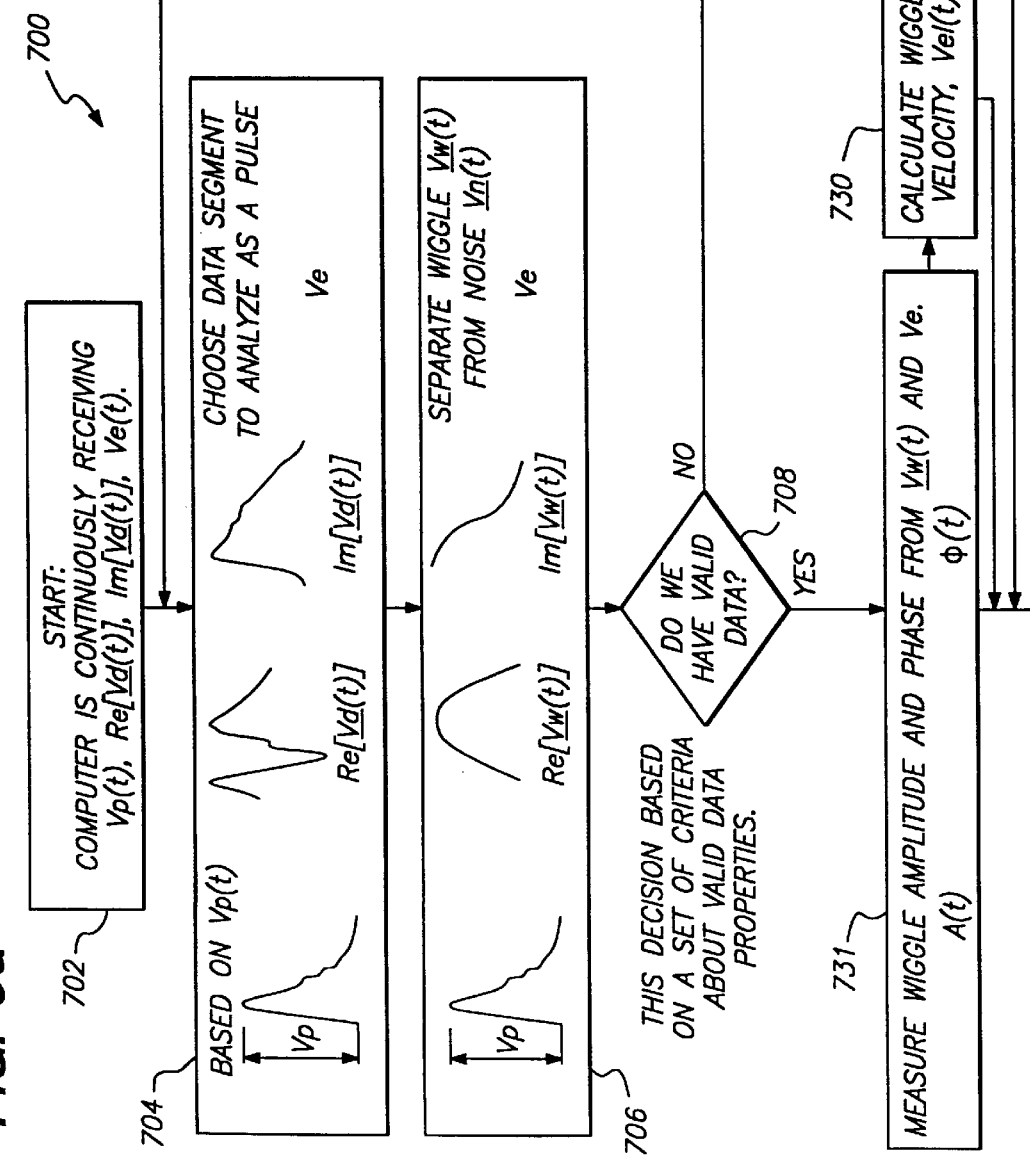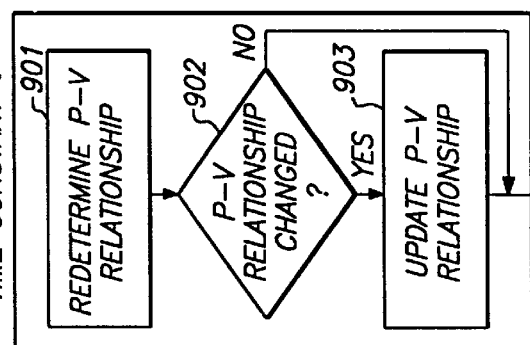

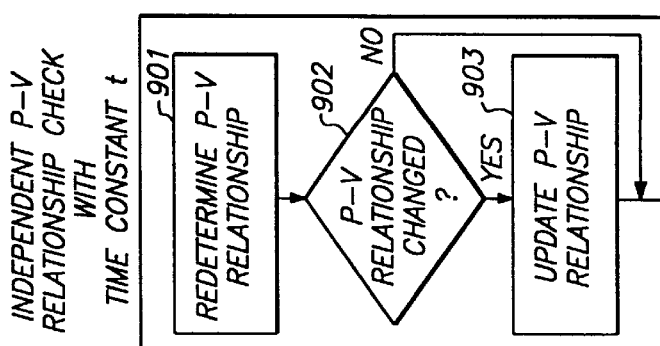
FIG. 10
| FIG. 10a |
| FIG. 10b |
FIG. 10a   COMPUTER DATA PROCESSING AND CONTROL
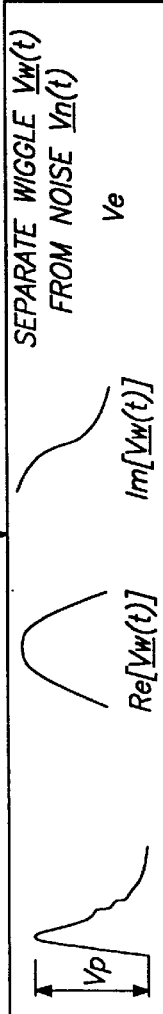

APPARATUS AND METHOD FOR MEASURING AN INDUCED PERTURBATION TO DETERMINE A PHYSICAL CONDITION OF THE HUMAN ARTERIAL SYSTEM

RELATED APPLICATIONS

This application is a continuation in part of the following patent applications and incorporates these applications by reference:

Caro, U.S. Ser. No. 08/228,213 filed on Apr. 15, 1994; now U.S. Pat. No. 5,590,649 and Caro, Apparatus and Method for Measuring an Induced Pertubration to Determine a Physical Condition of the Human Arterial System, U.S. Provisional Application No. 60/605748 filed on Oct. 20, 1995 (Atty Docket No. A-59155-3).

FIELD

The present invention relates to an apparatus and method for noninvasively providing a determination of a patient's physical condition and other clinically important parameters. In particular, the invention relates to an apparatus and method for measuring an induced perturbation to determine a physical condition of the human arterial system.

BACKGROUND

Blood pressure is the force within the arterial system of an individual that ensures the flow of blood and delivery of oxygen and nutrients to the tissue. Prolonged reduction or loss of pressure severely limits the amount of tissue perfusion and could therefore result in damage to or even death of the tissue. Although some tissues can tolerate hypoperfusion for long periods of time, the brain, heart and kidneys are very sensitive to a reduction in blood flow. The arteries are relied upon to provide the blood to the brain and other organs. Cardiovascular disease often results in a hardening of the arteries. When the arteries are hardened, the arteries are often incapable of providing sufficient blood to the various organs. Cardiovascular disease is a common disease in humans, and is a leading cause of premature death.

Two of the most important diseases of the cardiovascular system are hypertension, where the patient has elevated blood pressure which causes chronic systemic damage in the circulatory system, and arteriosclerosis, where a change in the physical composition of arteries leads to partial or complete arterial occlusion and restriction of the supply of blood borne nutrients to critical organs such as the heart and brain.

A great need exists to identify people at risk for these two diseases early on so as to allow for the implementation of various disease prevention strategies. Furthermore, once the disease is under treatment it is desirable to have a mechanism for monitoring the disease's progression in order to appropriately titrate the treatment.

In hypertension and in arteriosclerosis, advancing disease is associated with a progressive change in the physical properties of various arteries in the cardiovascular system. For example, hypertension is associated with the physical hardening of conduit arteries where arteries such as the carotid artery become increasingly stiff as the disease progresses. Arteriosclerosis commonly results in a hardening of peripheral arteries where arteries such as those in the leg become built up with calcified or fibrous deposits on the wall of the artery.

Contemporary medical consensus is that a device that can measure the stiffness of the arterial system in some way would have many uses in the diagnosis and treatment of hypertension and arteriosclerosis. As an example, the observation of peripheral arterial stiffness could indicate early stages of cardiovascular disease. For patients undergoing treatment for hypertension using blood pressure lowering drugs, the optimum drug regime could be determined by monitoring the degree of initial arterial stiffness and adjusting therapy to achieve a certain modification of that stiffness.

If a cheap, noninvasive device was available for monitoring human arterial stiffness, the device could possibly be used as a screening tool to determine human candidates who would most benefit from more expensive or invasive diagnostic procedures, as well as an adjunct to treatment of the disease. The present invention describes such an apparatus and method for making such a measurement of the physical properties of the arterial system.

RELATED ART

A number of studies have demonstrated a relationship between a propagation velocity of the naturally occurring blood pressure wave in the arterial system and arterial mechanical properties. One study related arterial pulse wave velocity to aortic stiffening. D. Farrar, Aortic Pulse Wave Velocity, *Elasticity, and Composition in a Nonhuman Primate Model of Atherosclerosis,* Circulation Res., vol. 43, no. 1, p. 52 (July 1978). Another study related arterial pulse wave velocity to the effect of drugs. T. Latson, *Effect of Nitroglycerin or Aortic Impedance, Diameter, and Pulse Wave Velocity,* Circulation Res., vol. 62, no. 5, p. 884 (May 1988). Yet another study related arterial pulse wave velocity to the effects of obesity and disease. J. Toto-Moukouo, *Pulse Wave Velocity in Patients with Obesity and Hypertension,* Am. Heart J., vol. 112, no. 1, p. 136 (July 1986).

The velocity of the naturally occurring blood pressure wave is influenced by the differing properties of the various segments of the arterial system through which it propagates on its way to the periphery. Measurements of the velocity made over significant distances (such as from the heart to the radial artery) can be made, but the velocity is then dependent on some average of the differing arterial properties of the arteries along the propagation path. Measurement of the velocity of the naturally occurring pulse over short distances such as over a small segment of the radial artery, are error prone due to the long duration of the pulse with respect to the time taken for its propagation. For these reasons it is difficult to use the natural pulse wave velocity as a reliable indicator of arterial physical condition.

Techniques for diagnosing and treating cardiovascular disease are described in U.S. Pat. Nos. 5,054,493; 5,211,177; and 5,316,004, where analysis of the waveform of the blood pressure pulse shape, detected at a peripheral artery such as the radial artery, is used to determine the compliance of an idealized model of the arterial system. That systemic compliance might have some useful relationship to systemic disease in the patient. Unlike the invention described here, in which measurements of arterial properties are made that apply to a specific arterial segment, this analysis involves determination of a value of compliance that is a form of averaged compliance representative of the entire system. Furthermore, the large amplitude of the natural pressure pulse allows various nonlinearities in the propagation equations to become important, thus rendering an analysis complex.

Another technique is described in U.S. Pat. No. 5,152,297, where arterial diameter and pressure are simultaneously measured and the elastic properties of the artery are measured therefrom.

In a study described by M. Anliker, *Dispersion and Attenuation of Small Artificial Pressure Waves in the Canine Aorta,* Circulation Res., vol. 23, p. 539 (October 1968), high frequency small-signal pressure perturbations were introduced into the arteries of dogs and the velocity of propagation was measured using an invasive pressure detector placed in the artery. The possibility of using these measurements to determine various physical properties of the arterial system is discussed. However, Anliker employs an invasive technique that has obvious drawbacks including infection and healing consequences.

OBJECTS AND SUMMARY

The present invention relates to an apparatus and method for noninvasively providing a determination of a patient's physical condition and other clinically important parameters. In particular, the invention relates to an apparatus and method for measuring an induced perturbation to determine a physical condition of the human arterial system.

An object of the invention is to induce a perturbation into a patient's blood or blood vessel and to noninvasively measure the perturbation to determine the patient's physical condition.

A related object is to filter the noninvasive sensor signal into components including a natural component, an induced component and a noise component, and to process the components to determine the patient's physical condition.

A further related object is to determine a relationship between a property of an induced perturbation and a property of a physiological parameter.

In the parent patent applications of Caro et al, techniques are described for the measurement of physiological parameters such as blood pressure, arterial elasticity, cardiac output, and other parameters. As part of those techniques, a procedure is described to determine a relationship between a patient's blood pressure P and the velocity of propagation Vel of an induced high frequency pressure perturbation along the artery. This relationship can have various forms and can be described generally as velocity equation:

$$Vel = f(P)$$

where f(P) is a function of pressure. An important step in the Caro techniques is the determination of the nature of the function f over a range of pressure in a given patient. In the Caro techniques, the relationship of the velocity equation was used to determine pressure following a measurement of velocity Vel. The present invention employs the information contained in the form of the function f to determine information relating to the physical condition of the arterial system.

The information regarding the physical condition of the arterial system can then be used to generate an output that can be used by health care personnel in the diagnosis and management of diseases such as cardiovascular disease.

A monitor for determining a patient's physical condition includes a calibration device configured to provide a calibration signal representative of a patient's physiological parameter. An exciter is positioned over a blood vessel of the patient for inducing a transmitted exciter waveform into the patient. A noninvasive sensor is positioned over the blood vessel, where the noninvasive sensor is configured to sense a hemoparameter and to generate a noninvasive sensor signal representative of the hemoparameter containing a component of a physiological parameter waveform and a component of a received exciter waveform. In this context, a hemoparameter is defined as any physiological parameter related to vessel blood such as pressure, flow, volume, velocity, blood vessel wall motion, blood vessel wall position and other related parameters. A processor is configured to determine a relationship between a property of the received exciter waveform and a property of the physiological parameter. The processor is connected to receive the calibration signal and the noninvasive sensor signal, and the processor is configured to process the calibration signal and the noninvasive sensor signal to determine a physical property of the patient in order to provide a condition signal related to the patient's physical condition.

In an exemplary embodiment, the physical property is arterial stiffness that represents a physical condition such as cardiovascular disease, however, many additional physical property can be measured and determined such as arterial elasticity, arterial thickness, arterial wall compliance and other properties that can provide information for determining the patient's physical condition.

Also, in an exemplary embodiment, the physiological parameter measured is blood pressure, however, the present invention can also be used to analyze and track other physiological parameters such as vascular wall compliance, strength of ventricular contractions, vascular resistance, fluid volume, cardiac output, myocardial contractility and other related parameters.

BRIEF DESCRIPTION OF THE FIGURES

Additional advantages of the invention will become apparent upon reading the following detailed description and upon reference to the drawings, in which:

FIG. 6, 6a–b depict a processing flow chart according to one embodiment of the invention;

FIGS. 8, 9a–b depict a processing flow chart according to another embodiment of the invention;

FIGS. 10a–b depict a processing flow chart according to another embodiment of the invention;

| GLOSSARY | |
|---|---|
| $P_D$ | diastolic blood pressure |
| $P_{D0}$ | diastolic blood pressure at calibration |

-continued

GLOSSARY

| | |
|---|---|
| $P_S$ | systolic blood pressure |
| $P_P$ | pulse pressure |
| $P_W$ | exciter waveform pressure |
| $V_d$ | received exciter waveform |
| $V_W$ | signal exciter waveform |
| $V_n$ | noise waveform |
| $V_e$ | exciter sensor signal (transmitted exciter waveform) |
| $V_P$ | detected pulsatile voltage |
| $\Phi_W$ | exciter signal phase |
| $\Phi W_D$ | exciter signal phase at diastole |
| Vel(t) | exciter signal velocity |
| $Vel_D$ | exciter signal velocity at diastole |
| $Vel_S$ | exciter signal velocity at systole |

DETAILED DESCRIPTION

The present invention relates to an apparatus and method for noninvasively providing a determination of a patient's physical condition and other clinically important parameters. In particular, the invention relates to an apparatus and method for measuring an induced perturbation to determine a physical condition of the human arterial system.

A preferred embodiment concentrates on the physical property of arterial stiffness that represents a physical condition such as cardiovascular disease, however, many additional physical properties can be measured and determined such as arterial elasticity, arterial thickness, arterial wall compliance and other properties that can provide information for determining the patient's physical condition. Also, the preferred embodiment concentrates on the physiological parameter of blood pressure, however, many additional physiological parameters can be measured with the present invention including vascular wall compliance, ventricular contractions, vascular resistance, fluid volume, cardiac output, myocardial contractility and other related parameters. Those skilled in the art will appreciate that various changes and modifications can be made to the preferred embodiment while remaining within the scope of the present invention. As used herein, the term continuous means that the physiological parameter of interest is determined over a period of time, such as during the course of surgery. The implementation of portions of the invention in a digital computer is performed by sampling various input signals and performing the described procedures on a set of samples. Hence, a periodic determination of the physiological parameter of interest is within the definition of the term continuous.

Figure 1:
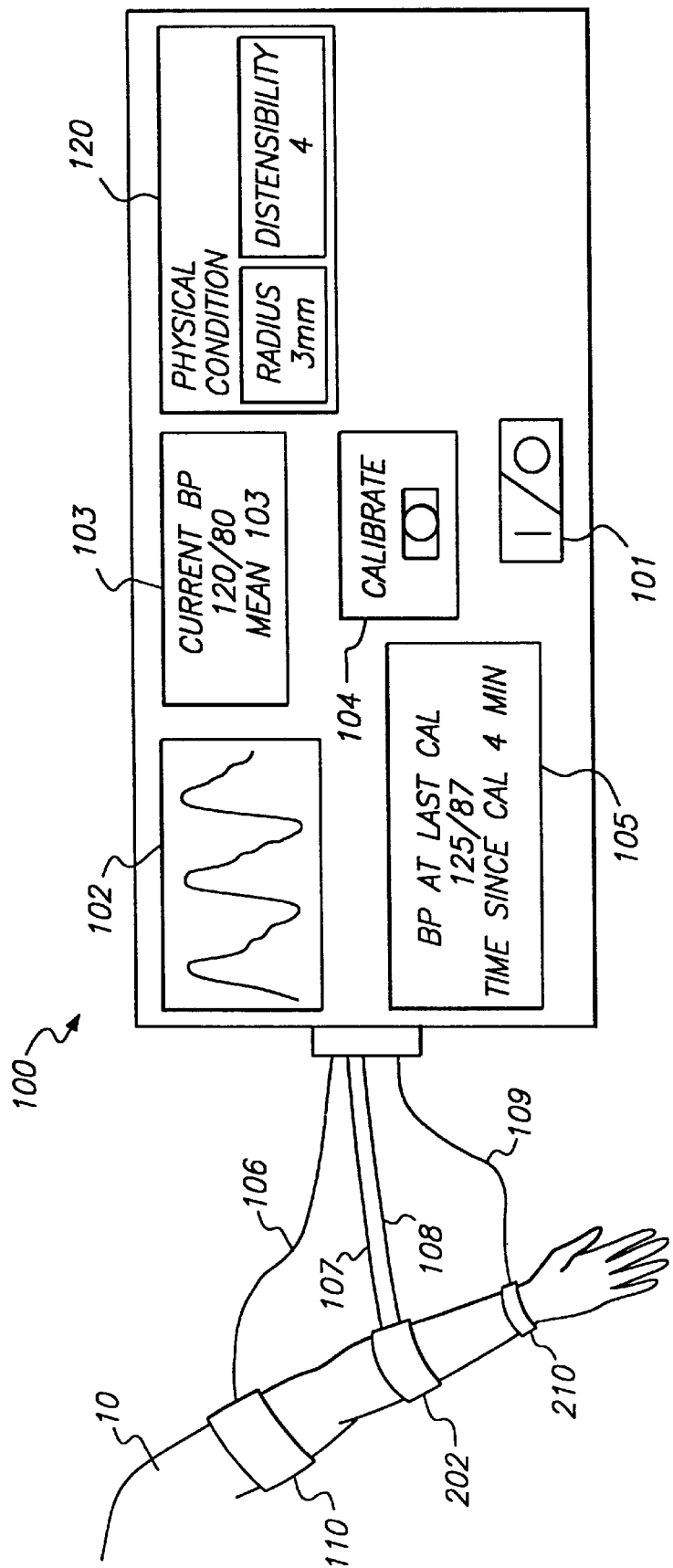
FIG. 1 depicts the present invention attached to a patient.

FIG. 1 illustrates the components and configuration of the preferred embodiment. Oscillometric cuff 110 is connected to processor 100 via wire 106, and cuff 110 is responsive to processor 100 during an initial calibration step. Oscillometric cuff operation, which is known in the art, involves an automated procedure for obtaining a blood pressure signal. The general procedure is given for clarity but is not crucial to the invention.

First, an occlusive cuff is pressurized around the patient's upper arm to abate the blood flow. Then, as the pressure is slowly reduced, a transducer senses when the blood flow begins and this pressure is recorded as the systolic pressure. As the pressure is further reduced, the transducer similarly detects the pressure when full blood flow is restored and this pressure is recorded as the diastolic pressure. The signals representing pressure are delivered, via wire 106, to processor 100 for storage. An alternative blood pressure measurement technique such as manual or automated sphygmomanometry using Korotkoff sounds or "return to flow" techniques, could also be used. A manual measurement can be provided, for example, using a keypad. Whatever measurement technique is used, a calibration device provides a calibration signal representative of the patient's physiological parameter. In this respect, the calibration device is broadly defined to include automated or manual measurements.

FIG. 1 shows an exciter 202 attached to the patient's forearm above the radial artery. The exciter 202 is a device for inducing a perturbation of the patient's body tissue, and is controlled by the processor 100 via tube 107.

Figure 2:
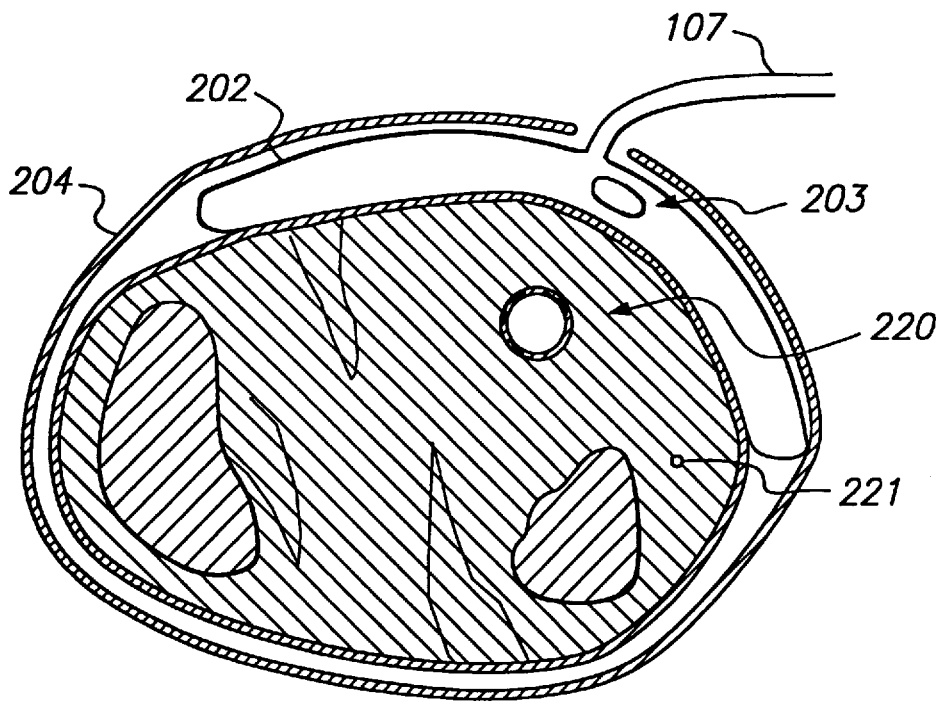
FIG. 2 depicts an exciter attached to a patient.

FIG. 2 shows a cross section of the exciter and its components. The exciter 202 is an inflatable bag attached to the processor via air tube 107. It is fixed in place near an accessible artery 220 by holddown device 204 which can be a buckle, adhesive strap or other device. There is also an exciter sensor 203 disposed within the exciter to generate a reference signal indicative of the perturbation source waveform, and to deliver the signal to the processor via wire 108. This signal is used as a reference signal by the processor (explained below).

As mentioned above, processor 100 is attached to the exciter via tube 107. The processor 100 controls the pressure in exciter 202 with a transducer and diaphragm. A transducer is a device that transforms an electrical signal to physical movement, and a diaphragm is a flexible material attached to the transducer for amplifying the movement. An example of this combination is a loudspeaker. The diaphragm forms part of an airtight enclosure connected to air tube 107 and an input to initialize the pressure. It will be clear to one skilled in the art that the transducer and air tube 107 and exciter 202 can be miniaturized and combined into a single exciter element capable of acting as a vibrating air filled bag connected to the processor by an electrical drive signal alone, in the case that a source of substantially constant pressure such as a spring is included in the exciter, or by an electrical drive signal and connection to a source of substantially constant pressure for the bag.

In operation, the pressure is initially established via the initialization input and then the pressure is varied by an electrical signal delivered to the transducer; the diaphragm produces pressure variations in the tube in response to the transducer movement. The result is that the processor, by delivering an oscillating electrical signal to the transducer, causes oscillating exciter pressure. The exciter responds by perturbing the patient's tissue and inducing a transmitted exciter waveform into the patient.

The perturbation excites the tissue 221 and blood vessel 220 below the exciter and causes the transmitted exciter waveform to radiate within the patient's body, at least a portion of which travels along the blood filled vessel. The excitation waveform can be sinusoidal, square, triangular, or of any suitable shape. Experiments conducted to determine a range of satisfactory perturbation frequencies found that the range of 20–1000Hz works well. It is anticipated that frequencies of lesser than 20Hz and greater than 1000 Hz will also work well, and it is intended that this specification cover all frequencies insofar as the present invention is novel.

FIG. 1 further shows a noninvasive sensor 210 placed at a distance from the exciter on the patient's wrist. The noninvasive sensor is connected to the processor 100 via wire 109.

Figure 3:
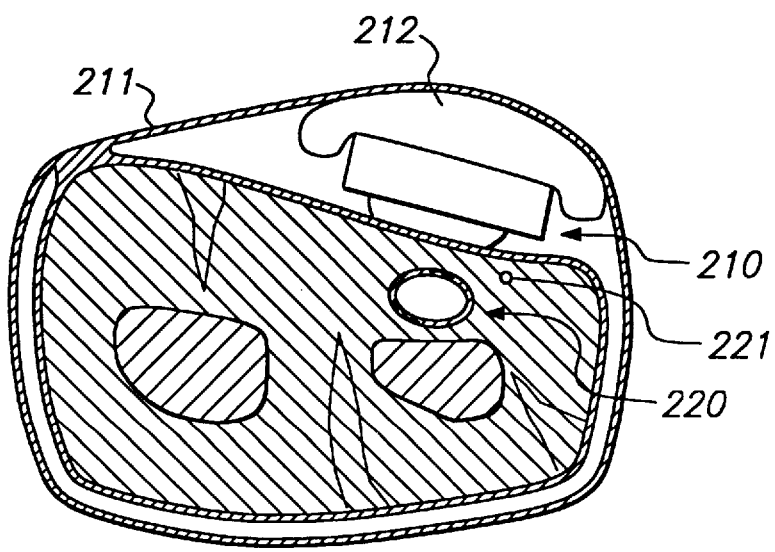
FIG. 3 depicts a noninvasive sensor attached to a patient.

FIG. 3 shows a cut-away view of the noninvasive sensor 210 placed over the same radial artery 220 as the exciter. The sensor 210 is fixed in place near the artery 220 by holddown device 211 which can be a buckle, adhesive strap or other device. The holddown device 211 also includes a baffle 212 to reduce noise, where the baffle is a pneumatic bag pressurized to hold the sensor 210 at a constant pressure against the patient, for example at a pressure of 10 mm Hg. Alternately, baffle 212 can be any suitable device such as a spring or foam pad.

The noninvasive sensor 210 is responsive to at least one hemoparameter of the patient and generates a signal in response thereto. In this context, a hemoparameter is defined as any physiological parameter related to vessel blood such as pressure, flow, volume, velocity, blood vessel wall motion, blood vessel wall position and other related parameters. In the preferred embodiment a piezoelectric sensor is used to sense arterial wall displacement, which is directly influenced by blood pressure.

As is shown, the sensor is positioned over the radial artery 220 and it is responsive to pressure variations therein; as the pressure increases, the piezoelectric material deforms and generates a signal corresponding to the deformation. The signal is delivered to the processor 100 via wire 109.

FIG. 1 also shows the processor 100 that has a control panel for communicating information with the user. A power switch 101 is for turning the unit on. A waveform output monitor 102 displays the continuous blood pressure waveform for medical personnel to see. This waveform is scaled to the pressures determined by the processor, and output to the monitor. A digital display 103 informs the user of the current blood pressure; there is a systolic over diastolic and mean pressure shown. A calibrate button 104 permits the user to calibrate the processor at any time, by pressing the button. The calibration display 105 shows the user the blood pressure at the most recent calibration, and also the elapsed time since calibration. A physical condition display 120 is also provided to show the patient's physical condition. The patient's physical condition is determined based on procedures described below, but for example can include artery radius and arterial distensibility. The processor maintains a record of all transactions that occur during patient monitoring including calibration blood pressure, calibration times, continuous blood pressure and other parameters, and it is anticipated that additional information can be stored by the processor and displayed on the control panel.

Turning to the noninvasive sensor signal, in addition to a natural hemoparameter, the noninvasive sensor signal contains a component indicative of the exciter waveform traveling through the patient. Although the exciter component is designed to be small in comparison to the natural hemoparameter, it contains valuable information. Therefore, the processor is used to separate the exciter waveform from the natural hemoparameter, and to quantify the respective components to determine the patient's blood pressure.

Figure 4A:
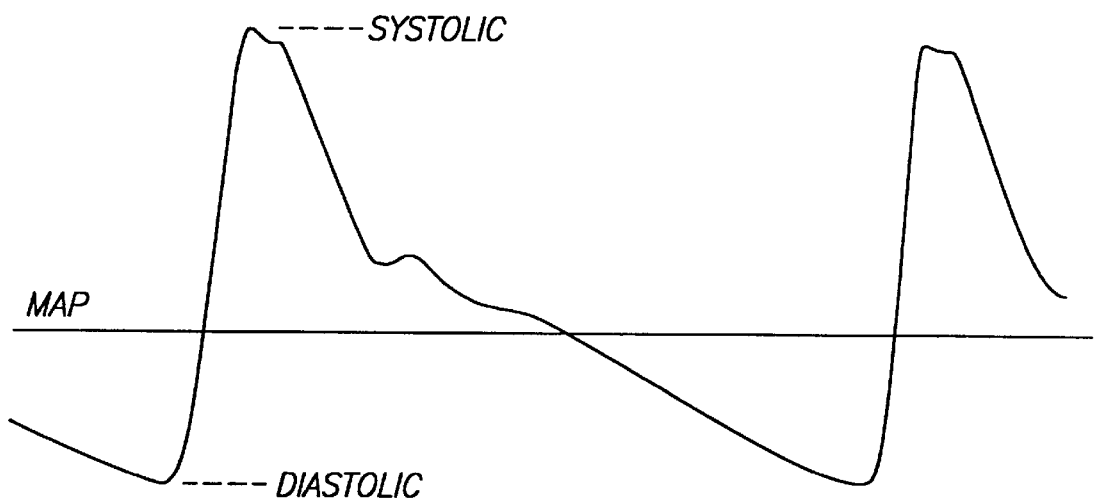
FIG. 4a depicts a blood pressure waveform.

FIG. 4a shows a natural blood pressure waveform where the minimum represents the diastolic pressure and the maximum represents the systolic pressure. This waveform has a mean arterial pressure (MAP) that is a convenient reference for purposes of determining the DC offset of the waveform. Example pressure values are 90 mm Hg diastolic and 120 mm Hg systolic respectively with a MAP DC offset of 80 mm Hg.

Figure 4B:
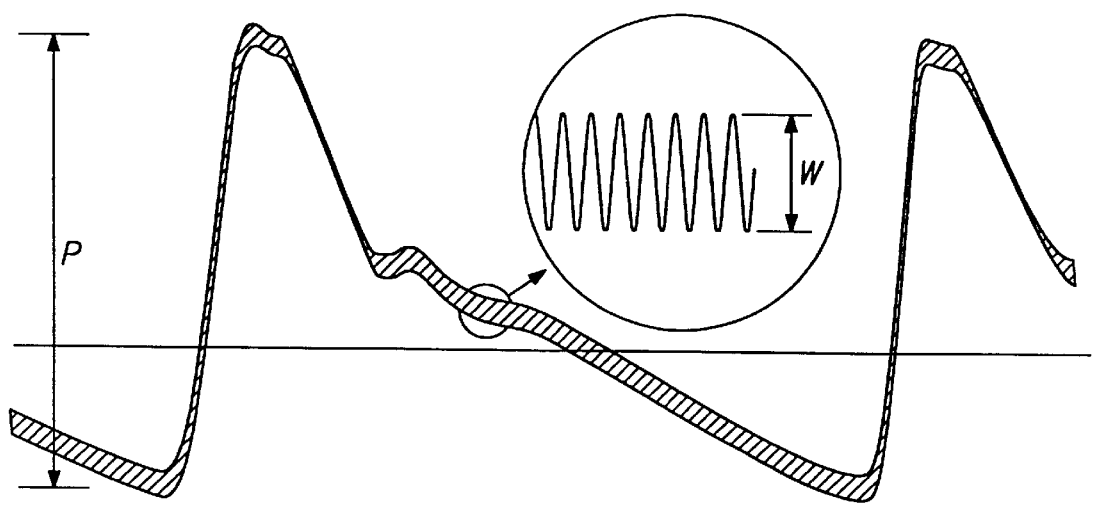
FIG. 4b depicts a blood pressure waveform with an exciter waveform superimposed thereon.

FIG. 4b shows an operational illustration of the arterial waveform; an exciter waveform superimposed on a natural blood pressure waveform. The exciter induces the exciter waveform into the arterial blood at a first location and the exciter waveform becomes superimposed on the natural waveform. Since the exciter waveform is small compared to the patient's natural waveform, the natural waveform dominates as shown in FIG. 4b. As mentioned above, the noninvasive sensor signal contains information regarding both the natural waveform and the exciter waveform. The processor 100 is designed to separate the constituent components of the noninvasive sensor signal to continuously determine the patient's blood pressure, as is discussed below.

Figure 5:
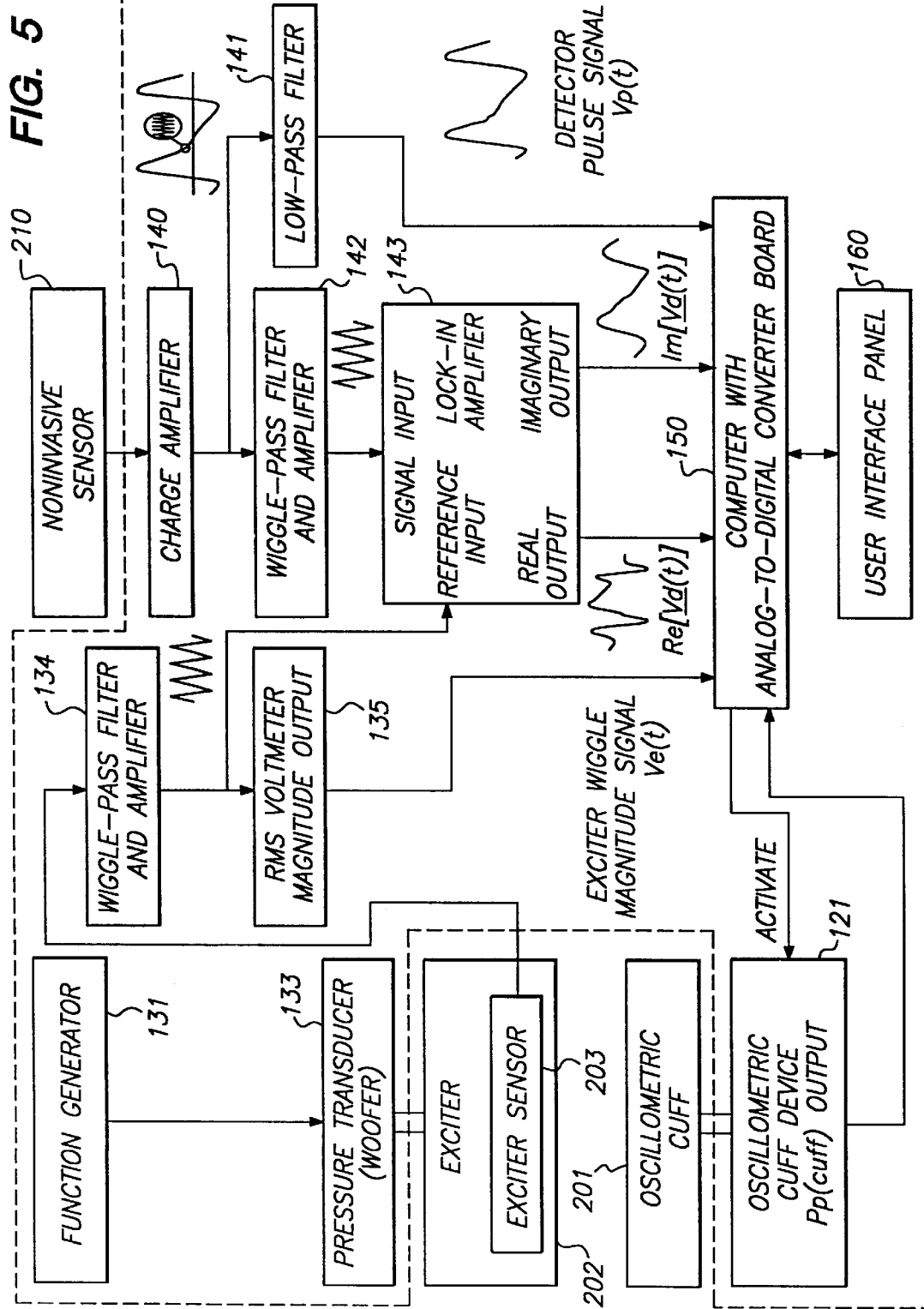
FIG. 5 depicts a schematic diagram of the present invention.

FIG. 5 depicts a schematic diagram of the preferred embodiment. There is an oscillometric cuff controller 121 for controlling the oscillometric cuff and determining the readings therefrom to generate a signal representing the patient's blood pressure. There is an induced wave frequency generator 131 coupled to a pressure transducer 133 that transforms an electrical input to a pressure output. The transducer output is connected to the exciter 202 and controls the exciter's oscillations for inducing the exciter waveform into the patient's arterial blood.

The output of the exciter sensor 203 is fed to a band pass filter 134. This filter 134 separates the high frequency signal responsive to the transducer pressure and delivers the resulting signal to RMS meter 135 and to lock-in amplifier 143 reference input. In the preferred embodiment, the RMS meter output is sampled at a rate of 200 samples per second with a 14 bit resolution and delivered to computer 150. It is anticipated that the sampling rate and resolution can be varied with good results.

The output of the noninvasive sensor is fed to a charge amplifier 140 that delivers a resulting signal to a low pass filter 141 and a band pass filter 142. These filters separate the noninvasive sensor signal into two constituent components representing an uncalibrated natural blood pressure wave and a received exciter waveform respectively. The low pass filter output is sampled at a rate of 200 samples per second with 14 bit resolution and delivered to computer 150, and the band pass filter output is delivered to the lock-in amplifier 143 signal input.

The lock-in amplifier 143 receives inputs from band pass filter 134 as reference and band pass filter 142 as signal, which are the exciter sensor signal (transmitted exciter waveform) and noninvasive sensor exciter signal (received exciter waveform) respectively. The lock-in amplifier uses a technique known as phase sensitive detection to single out the component of the noninvasive sensor exciter signal at a specific reference frequency and phase, which is that of the exciter sensor signal. The amplifier 143 produces an internal, constant-amplitude sine wave that is the same frequency as the reference input and locked in phase with the reference input. This sine wave is then multiplied by the noninvasive sensor exciter signal and low-pass filtered to yield a signal proportional to the amplitude of the noninvasive sensor signal multiplied by the cosine of the phase difference between the noninvasive exciter signal and the reference. This is known as the in-phase or real output.

The amplifier 143 also produces an internal reference sine wave that is 90 degrees out-of-phase with the reference input. This sine wave is multiplied by the received exciter signal and low-pass filtered to yield a signal proportional to the amplitude of the noninvasive sensor signal multiplied by the sine of the phase difference between the noninvasive sensor exciter signal and the reference. This is known as quadrature or imaginary output. The amplifier 143 then provides the computer 150 with information regarding the real and imaginary components of the received exciter signal as referenced to the phase of the transmitted exciter signal.

Alternately, the amplifier can provide components representing the magnitude and phase of the received exciter signal. In the preferred embodiment, the amplifier output is sampled at a rate of 200 samples per second with a 14 bit resolution. It is anticipated that the sampling rate and resolution can be varied with good results.

The computer 150 receives input from the oscillometric cuff controller 121, RMS meter 135, low pass filter 141 and lock-in amplifier 150. The computer 150 also receives input from the user interface panel 160 and is responsible for updating control panel display information. The computer 150 executes procedures for further separating constituent components from the noninvasive sensor signal and attenuating the noninvasive sensor noise component as shown in FIG. 6.

While the processing system described in the embodiments involves the use of a lock-in amplifier 143, it will be clear to those persons skilled in the art that similar results can be achieved by frequency domain processing. For example, a Fourier transform can be performed on the various signals to be analyzed, and processing in the frequency domain can be further performed that is analogous to the described processing by the lock-in amplifier in the time domain. The various filtering steps described above can be advantageously performed in the frequency domain. Processing steps in the frequency domain are considered as falling within the general category of the analysis of the transfer function between the exciter sensor waveform and the noninvasive sensor waveform and are intended to be covered by the claims. The variety of techniques that are used in the art for the calculation of transfer functions are also applicable to this analysis.

PROCESS EXCITER WAVEFORM VELOCITY TO DETERMINE OFFSET SCALING AND EXCITER WAVEFORM AMPLITUDE TO DETERMINE GAIN SCALING

Figure 6A:
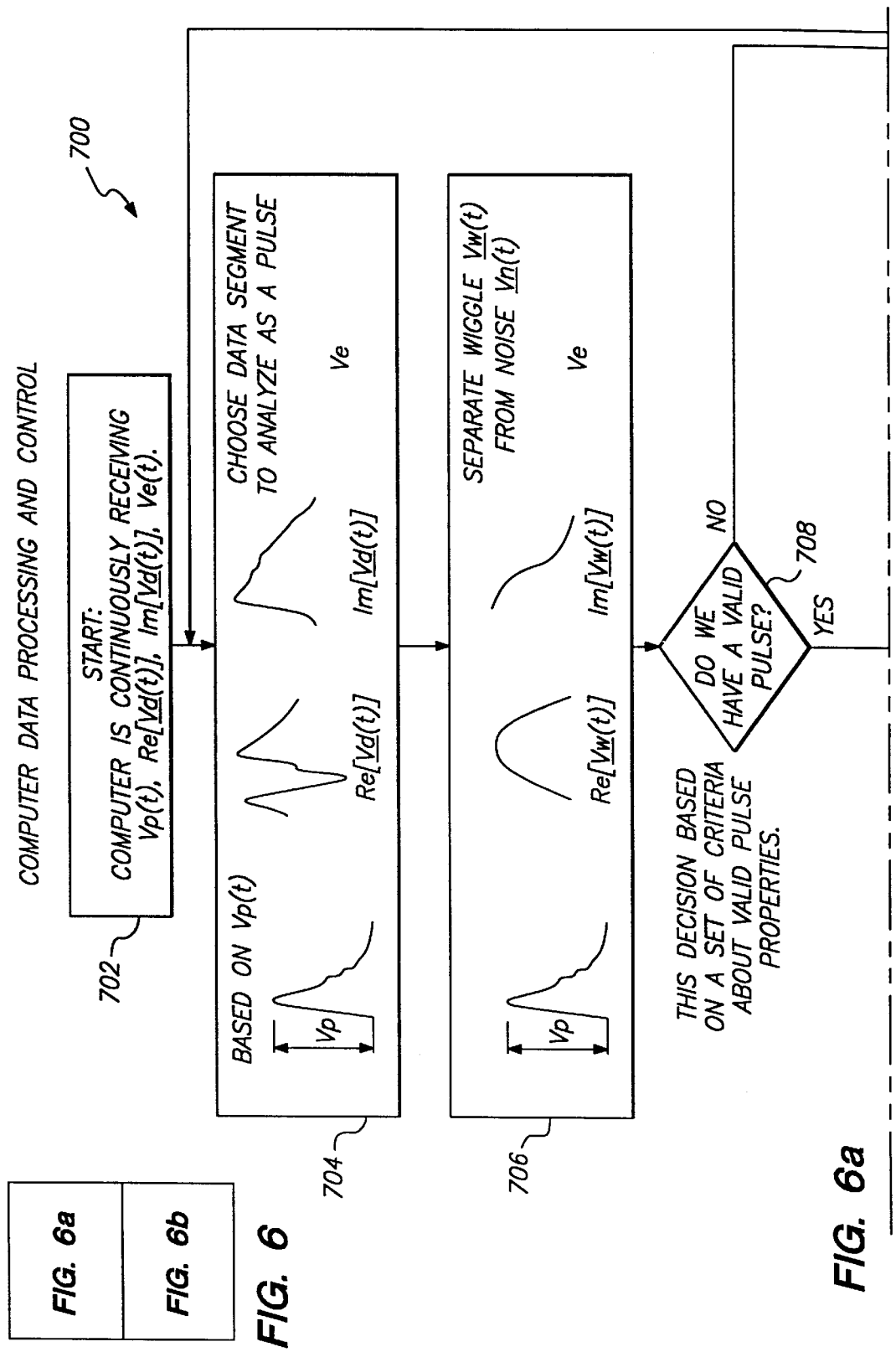
Figure 6B:
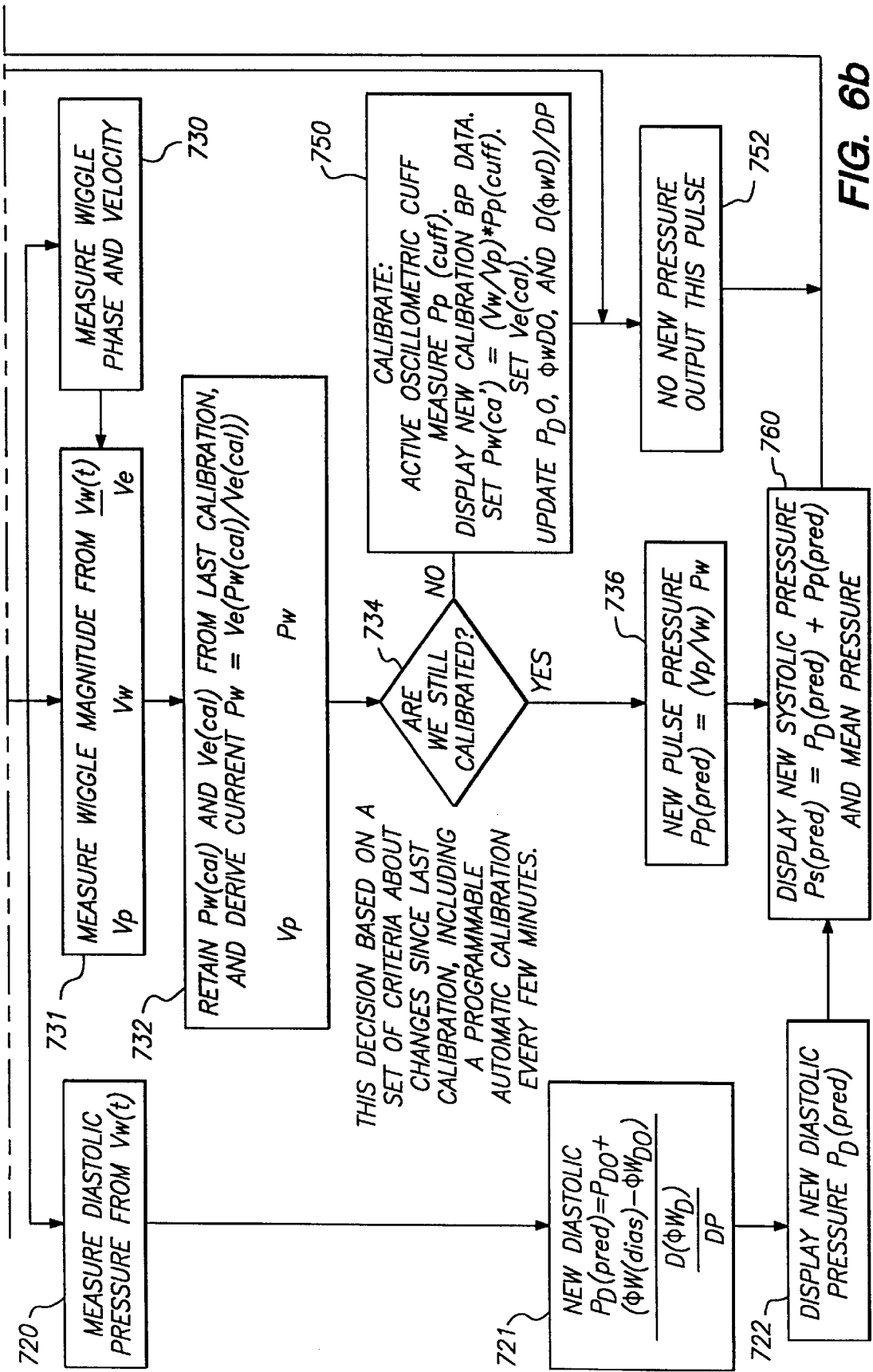

FIG. 6 is a processing flowchart that represents the operation of the FIG. 5 computer 150. The operation begins at step 702 with the receipt of an initial calibration measurement; noninvasive sensor signal and exciter sensor signal. Step 704 chooses the blood pressure waveform segment for pulse reference, which is important for continuity of measurement from pulse to pulse and for consistency over periods of time between calibration measurements. In this embodiment, the diastolic pressure (low-point) is chosen for purposes of simplicity, but any point of the waveform can be chosen such as the systolic pressure or mean arterial pressure (MAP). The choice of the segment will relate to the DC offset discussed below.

Step 706 is a filter step where the noninvasive sensor (received) exciter waveform is separated into signal and noise components. The noise components may have many sources, one of which is a signal derived from the exciter that travels to the noninvasive sensor by an alternate path, other than that along the artery taken by the signal of interest. Examples include bones conducting the exciter waveform and the surface tissue such as the skin conducting the exciter waveform. Additional sources of noise result from patient movement. Examples include voluntary patient motion as well as involuntary motion such as movement of the patient's limbs by a physician during surgery.

Figure 7A:
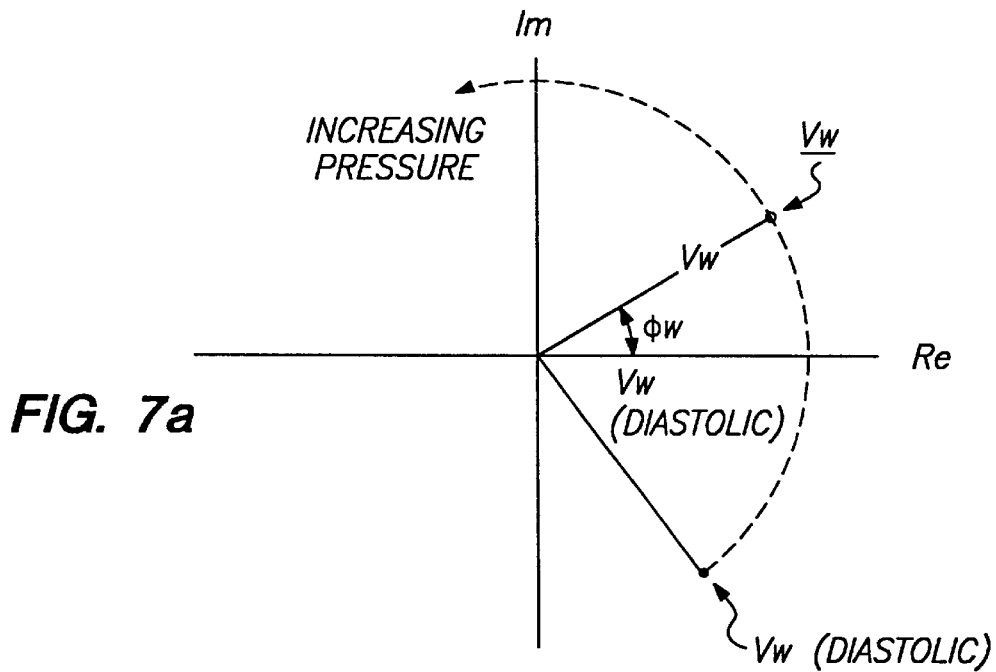
FIGS. 7a–c are graphical illustrations of the filter procedures of the present invention.
Figure 7B:
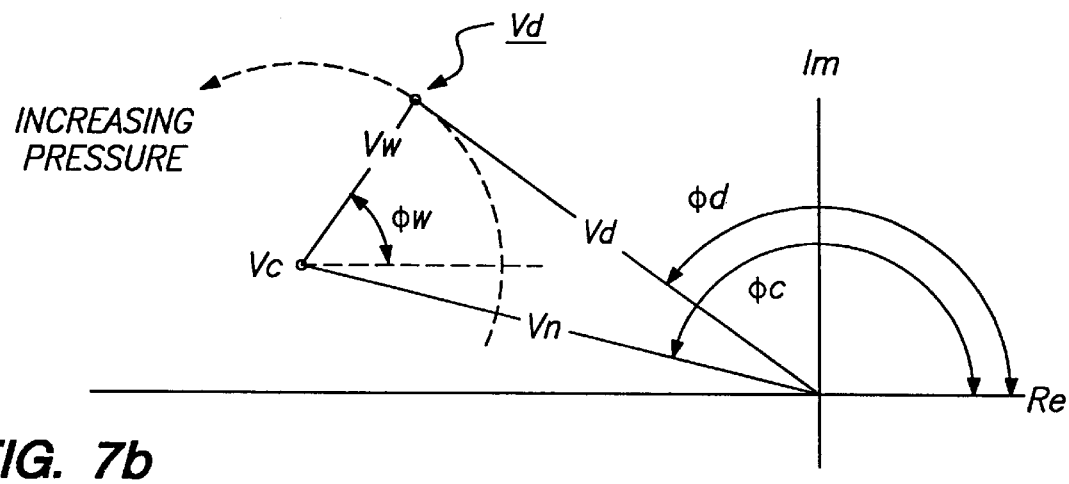
Figure 7C:
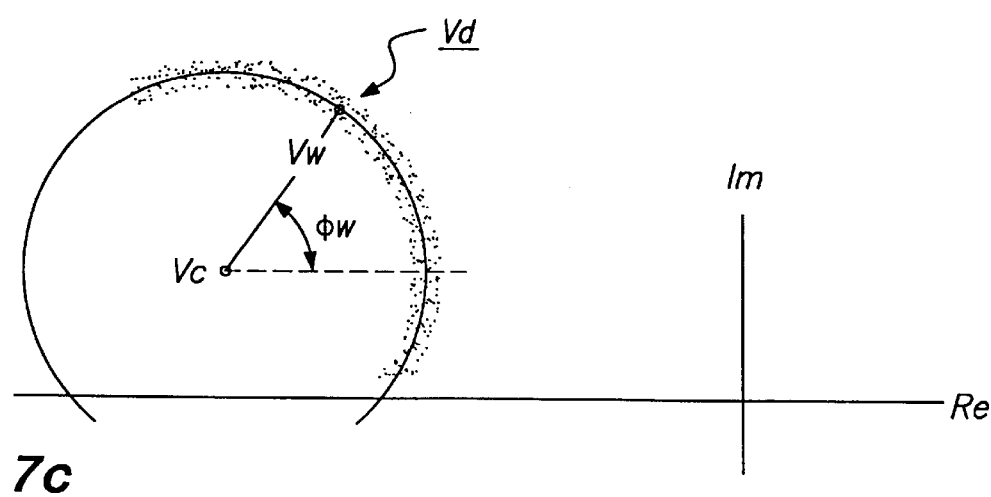

FIGS. 7a–c illustrate the principles of the received exciter signal filtering. During a natural pulse, the received exciter waveform $V_d$ is represented by a collection of points that are generated in the complex plane by the real and imaginary outputs of the lock-in amplifier 143 which is monitoring the noninvasive sensor signal. FIG. 7a represents the received exciter waveform $V_d$ in the absence of noise. In the absence of noise, $V_d$ is the same as vector $V_w(t)$ which has a magnitude and phase corresponding to the received exciter signal. During a pulse, the magnitude of $V_w(t)$ remains constant, but the angle periodically oscillates from a first angle representing a lesser pressure to a second angle representing a greater pressure. Note that in the absence of noise, the arc has a center at the origin.

FIG. 7b represents the received exciter waveform $V_d$ in the presence of noise, which is indicated by vector $V_n$. Vector $V_d$ has a magnitude and phase according to the noninvasive sensor exciter waveform plus noise. As can be seen in FIGS. 7b–c, vector $V_d(t)$ defines a collection of points forming an arc having a common point $V_c$ equidistant from each of the collection of points. The vector $V_w(t)$ from $V_c$ to the arc corresponds to the true magnitude and phase of the noninvasive signal exciter waveform. The vector $V_n$ represents noise and, once identified, can be removed from the noninvasive sensor waveform. The filter step removes the $V_n$ noise component and passes the $V_w(t)$ signal exciter component on to step 708.

In the above discussion, it was assumed for illustrative purposes that the magnitude of $V_w(t)$ remains constant over the time of a pulse. In some cases the attenuation of the exciter waveform as it propagates along the artery is pressure dependent, and in those cases the magnitude of $V_w(t)$ can vary during the pulse in a way that is correlated to pressure. Under such circumstances the shape of the figure traced out in the complex plane by the vector $V_d$ will deviate from a perfect circle segment. A typical shape is that of a spiral with a form that can be predicted theoretically. The functioning of this filter step under such circumstances is conceptually similar to that described above, except that the elimination of the noise vector $V_n$ must involve location of the origin of a spiral rather than of the center of a circle.

Step 708 determines if the pulse is valid. To do this, the processor checks the constituent components of the noninvasive sensor signal to insure that the components are within acceptable clinical norms of the patient. For example, the processor can determine whether the new pulse is similar to the prior pulse, and if so, the new pulse is valid.

Figure 8A:
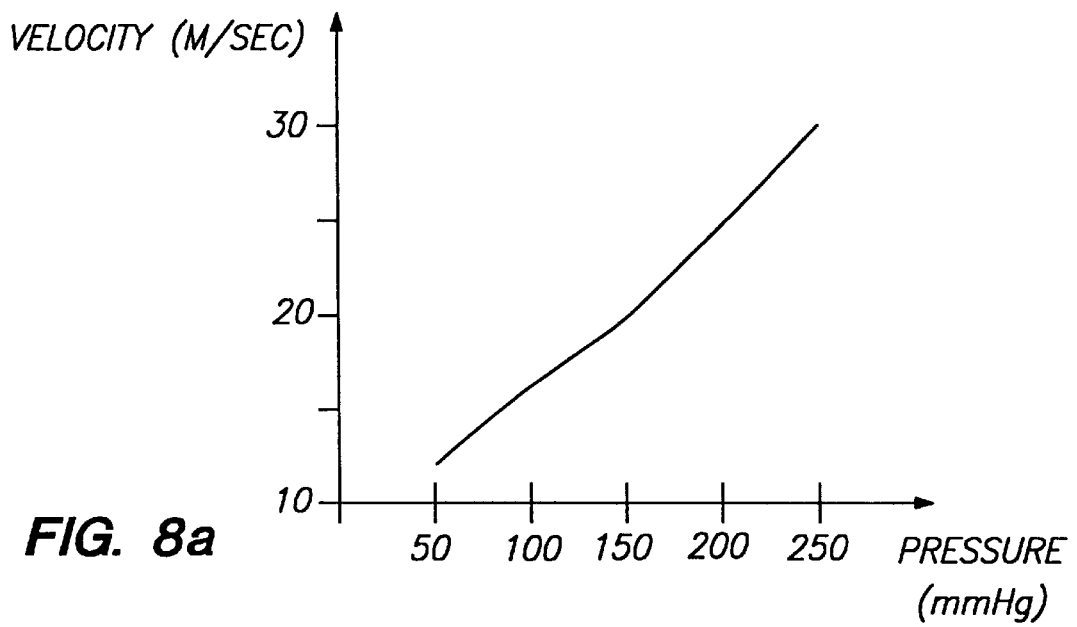
FIGS. 8a–c are graphical illustrations showing the relationships between the exciter waveform and blood pressure.
Figure 8B:
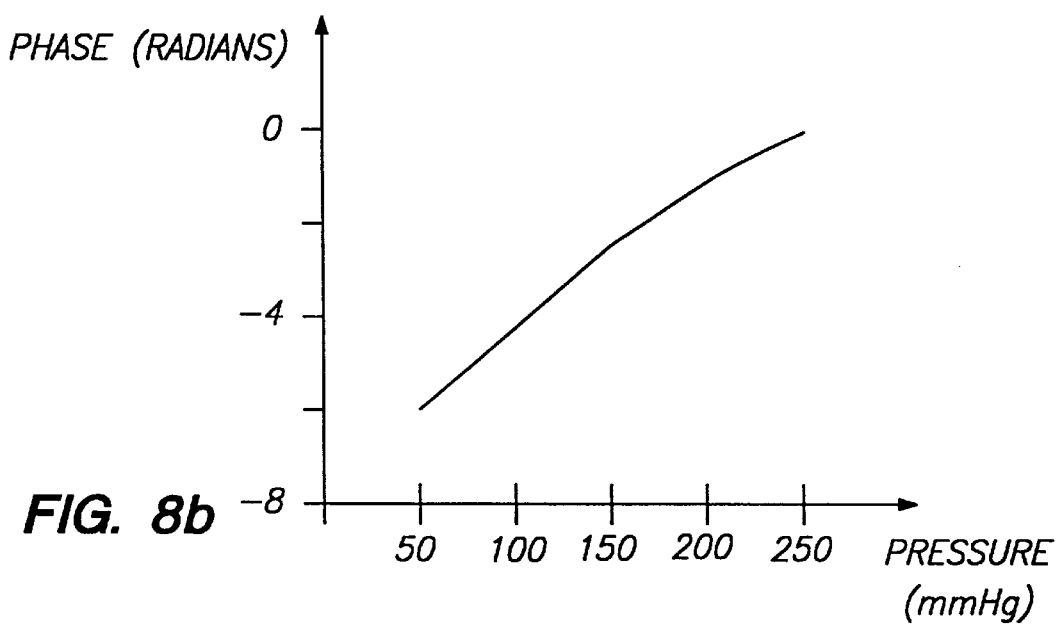
Figure 8C:
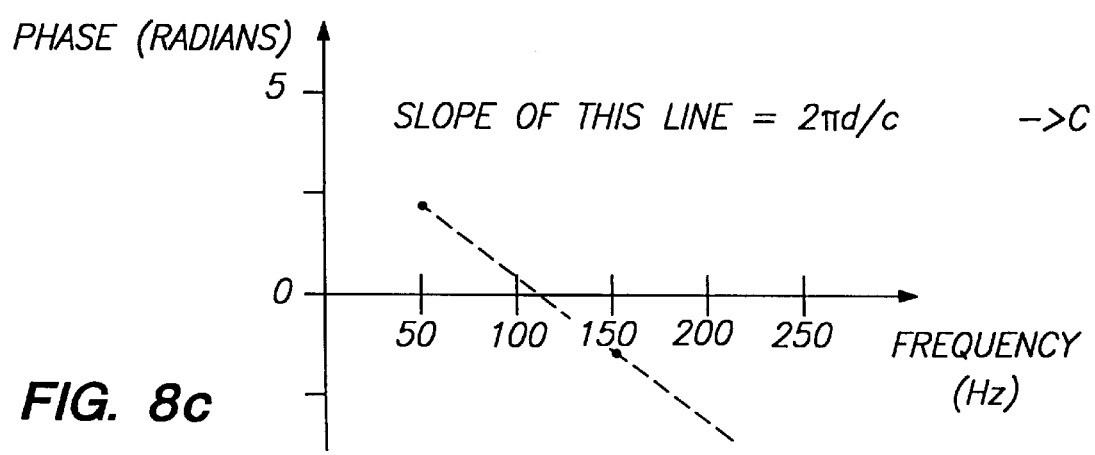

Step 720 processes the signal exciter waveform $V_w(t)$ to determine the DC offset. For convenience the diastole is used as the offset value, but any part of the waveform can be used. The processor determines the offset when the vector $V_w(t)$ reaches its lowest phase angle (i.e., the maximum clockwise angle of FIG. 7a); this is the diastole phase angle $\Phi_w(\text{dias})$. A calibration diastolic measurement is stored by the processor at calibration as $P_{D0}$. Also stored by the processor is a relationship denoting the relationship between the velocity of an exciter wave and blood pressure. This relationship is determined by reference to a sample of patients and is continuously updated by reference to the particular patient after each calibration measurement. FIG. 8a–c are graphical illustrations showing clinically determined relationships between the exciter waveform and blood pressure. FIG. 8b represents the relationship between phase and pressure at a frequency of 150Hz; other frequencies have relationships that are vertically offset from the line shown. The pressure-velocity relationship represents the storage of this graphical information either in a data table or by an analytical equation.

Step 721 determines the predicted diastolic pressure from the information in Step 720. The processor continuously determines the change in diastole from one pulse to the next by referencing the position of the signal exciter vector $V_w(t)$, at $\Phi_w(\text{dias})$, with respect to the stored pressure-velocity relationship. Moreover, the pressure-velocity relationship is continuously updated based on calibration measurement information gained from past calibrations of the patient.

A set of established relationships is used to develop and interpret information in the table and to relate the information to the sensor signal components. First, a known relationship exists between blood pressure and exciter waveform velocity. Also, at a given frequency many other relationships are known: a relationship exists between velocity and wavelength, the greater the velocity the longer the wavelength; and a relationship exists between wavelength and phase, a change in wavelength will result in a proportional change in phase. Hence, a relationship exists between blood pressure and phase, and a change in blood pressure will result in a proportional change in phase. This is the basis for the offset prediction.

With the stored calibration measurement plus the change in diastole, the new DC offset diastolic pressure is predicted $P_D(\text{pred})$. This prediction is made based on the diastolic pressure at calibration $P_{D0}$ plus the quotient of the phase difference between calibration $\Phi w_{D0}$ and the present time $\Phi w(\text{dias})$ and the pressure-velocity relationship stored in processor memory as rate of change of exciter waveform phase to pressure $d(\Phi w_D)/dP$.

$$P_D(\text{pred}) = P_{D0} + \frac{(\phi w(\text{dias}) - \phi w_{D_o})}{d(\phi w_D)/dP} \quad (1)$$

Step 722 displays the predicted diastolic pressure.

Step 730 determines the noninvasive sensor exciter waveform phase and velocity. This determination is made based on the comparison of the noninvasive sensor exciter waveform with the exciter sensor waveform.

Step 731 determines the noninvasive sensor exciter waveform amplitude from the noninvasive sensor signal.

Step 732 determines the exciter waveform pressure $P_w$ by multiplying the exciter sensor waveform magnitude $V_e$ by the ratio of the calibrated exciter waveform pressure $P_w(\text{cal})$ to the calibrated exciter sensor waveform magnitude $V_e(\text{cal})$.

$$P_w = V_e * \frac{P_w(\text{cal})}{V_e(\text{cal})} \quad (2)$$

In situations where a significant pressure variation can be observed in the attenuation of the exciter waveform as it propagates from exciter to detector, an additional multiplicative pressure dependent correction factor must be included in equation 2.

Step 734 determines if the calibration values are still valid. This determination can be based on many factors including the time since the last calibration, that the linearity of the pressure-velocity relationship is outside of a reliable range, determination by medical personnel that a new calibration is desired or other factors. As an example of these factors, the preferred embodiment provides user settable calibration times of 2, 5, 15, 30, 60 and 120 minutes, and could easily provide more. Moreover, the curve upon which the pressure is determined is piecewise linear with some degree of overall nonlinearity. If the processor 100 determines that the data is unreliable because the linear region is exceeded, the processor will initiate a calibration step. Finally, if the operator desires a calibration step, a button 104 is provided on the processor 100 for initiating calibration manually.

Step 736 predicts a new pulse pressure $P_p(\text{pred})$ by multiplying the exciter waveform pressure $P_w$ by the ratio of the detected pulsatile voltage $V_p$ to the detected exciter waveform magnitude $V_w$.

$$P_p(\text{pred}) = P_w * \left(\frac{V_p}{V_w}\right) \quad (3)$$

This prediction uses the noninvasive sensor exciter waveform to determine the pressure difference between the diastole and systole of the natural blood pressure waveform. For example, if a noninvasive sensor exciter magnitude $V_w$ of 0.3 V relates to a pressure variation $P_w$ of 1 mm Hg and the noninvasive sensor waveform $V_p$ varies from −6 V to +6 V, then the noninvasive sensor waveform represents a pulse pressure excursion $P_p(\text{pred})$ of 40 mm Hg.

Step 760 predicts a new systolic pressure $P_s(\text{pred})$ by adding the predicted diastolic $P_D(\text{pred})$ and pulse pressures $P_p(\text{pred})$.

$$P_s(\text{pred}) = P_D(\text{pred}) + P_p(\text{pred}) \quad (4)$$

In the above example if the diastole PD(pred) is 80 mm Hg (DC offset) and the pulse $P_p(\text{pred})$ represents a difference of 40 mm Hg then the new systolic $P_s(\text{pred})$ is 120 mm Hg. Then the new systolic pressure is displayed.

For display purposes the values determined for $P_s(\text{pred})$ and $P_D(\text{pred})$ can be displayed numerically. Similarly, the output waveform for display 102 can be displayed by scaling the noninvasive sensor natural blood pressure waveform prior to output using gain and offset scaling factors so that the output waveform has amplitude, $P_p(\text{pred})$, and DC offset, $P_D(\text{pred})$, equal to those predicted in the above process. The scaled output waveform signal can also be output to other instruments such as monitors, computers, processors and displays to be used for display, analysis or computational input.

Step 750 is taken when step 734 determines that the prior calibration is no longer reliable as described above. A calibration step activates the oscillometric cuff 201 and determines the patient's blood pressure, as described above. The processor 100 uses the calibration measurements to store updated pressure and waveform information relating to the DC offset, blood pressure waveform and exciter waveform. The updated variables include calibration pulse pressure $P_p(\text{cal})$, calibration exciter sensor waveform magnitude $V_s(\text{cal})$, diastolic pressure $P_{D0}$, diastolic exciter waveform phase $\Phi w_{D0}$, the rate of change of exciter waveform phase to pressure $d(\Phi w_D)/dP$ and calibration exciter waveform pressure $P_w(\text{cal})$.

$$P_w(\text{cal}) = P_p(\text{cal}) * \left(\frac{V_w}{V_p}\right) \quad (5)$$

PROCESS EXCITER WAVEFORM VELOCITY TO DETERMINE OFFSET SCALING AND GAIN SCALING

Figure 9B:
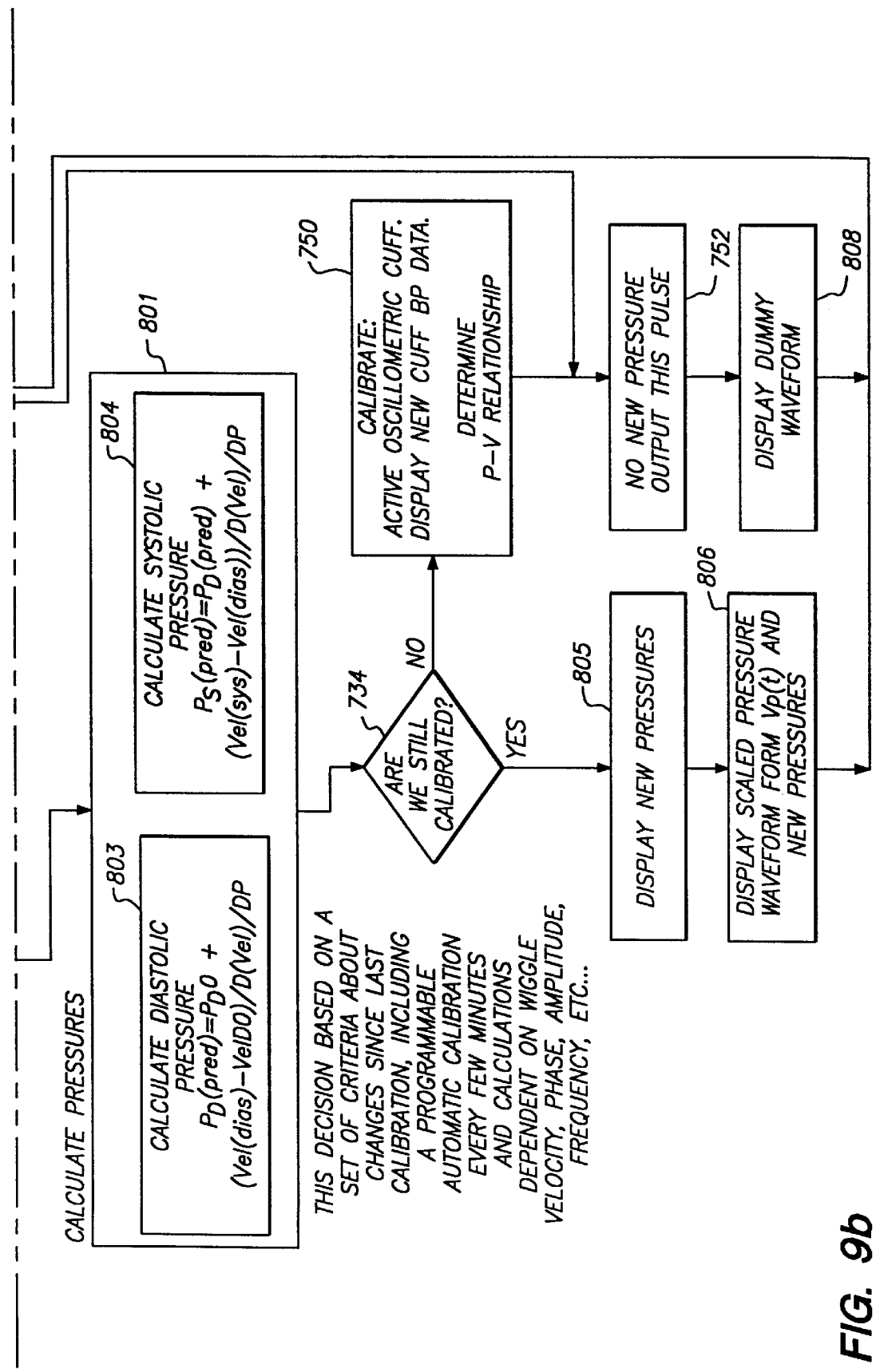

FIGS. 9a–b represent a modification to the previous embodiment. The initial processing steps 702, 704, 706, 708, 730 and 731 represented in the flow chart of FIG. 9 are substantially similar to those described in the previous embodiment depicted in FIG. 6. In step 730, exciter waveform velocity Vel(t) and the actual phase delay of the exciter waveform $\Phi(t)$ are related by the equation:

$$\Phi(t) = \Phi_0 - 2\pi df/Vel(t) \quad (6)$$

where frequency f and distance d between exciter and noninvasive sensor are known. The constant $\Phi_0$ is determined in advance either analytically or empirically, and is dependent on the details of the geometry of the apparatus.

Measurement of $\Phi(t)$ is generally made modulo $2\pi$, and so the measured phase $\Phi_m(t)$ is related to actual phase delay by the equation:

$$\Phi_m(t)=\Phi(t)+2n\pi \qquad (7)$$

where n is an integer also known as the cycle-number, typically in the range of 0–10. While correct deduction of propagation velocity requires a correct choice of n, a correct prediction of pressure using a pressure-velocity relation does not, so long as the same value of n is used in determining $\Phi(t)$ and in determining the pressure-velocity relationship. In such a case, velocity should be considered as a pseudo-velocity rather than an actual measure of exciter waveform propagation speed.

In step 730, therefore, use of the $\Phi(t)$ equations allows determination of the velocity, or pseudo-velocity, Vel(t) as a function of time. In step 801, the values of velocity at the systolic and diastolic points of the cardiac cycle are determined as $Vel_S$ and $Vel_D$. These correspond to the points of minimum and maximum phase delay or to the points of maximum and minimum amplitude of the naturally occurring blood pressure wave detected by the noninvasive sensor. Use of the pressure-velocity relationship stored in the processor is then made to transform the values of velocity at systolic and diastolic points in time to values of pressure. In step 803 the diastolic pressure is determined using the equation:

$$P_D(pred)=P_{D0}+(Vel_D-Vel_{D0})/(dVel/dP) \qquad (8)$$

Step 804 is performed to determine the predicted systolic pressure according to the relationship:

$$P_S(pred)=P_D(pred)+(Vel_S-Vel_D)/(dVel/dP) \qquad (9)$$

In this illustration the values of $P_S$ and $P_D$ are used to determine the pressure waveform. Similarly, other pairs of values, such as mean pressure and pulse pressure can also be used, and appropriate permutations of the predicted pressure. equations are anticipated by this description.

In step 805 the calculated pressures are displayed as numbers, with a typical display comprising display of mean, systolic and diastolic values of the pressure waveform in digital form, together with the observed pulse rate. The values of $P_D(pred)$ and $P_S(pred)$ are used to determine appropriate gain and DC offset scaling parameters by which the naturally occurring blood pressure waveform detected by the noninvasive sensor is scaled prior to output in step 806 as a time varying waveform, shown as 102 in FIG. 1.

As in the embodiment depicted in FIG. 6, step 750 involves a calibration step initiated when step 734 determines that the prior calibration is no longer reliable. During the performance of step 750 the pressure-velocity relationship is determined and stored in the processor in the form of a table or of an analytical relationship. During this process, it may be desirable to stop the output portion of the process as shown in step 752 and display a different signal, such as a blank screen, a dashed line display, a blinking display, a square wave, or some other distinguishable signal of calibration such as an audible tone. This step is represented as step 808 in FIG. 9.

PROCESS EXCITER WAVEFORM VELOCITY TO DETERMINE OUTPUT BLOOD PRESSURE WAVEFORM

In both of the previous two embodiments, values of gain Pp(pred) and offset $P_D(pred)$ are determined and used to scale the noninvasive sensor natural blood pressure waveform to provide a time varying output waveform representative of the patient's blood pressure. In this embodiment, the natural blood pressure waveform monitored by the noninvasive sensor is not used in the determination of the output blood pressure waveform. As in the previous embodiment, use is made of the relationship between velocity of the exciter waveform and the blood pressure of the patient to determine the blood pressure. Rather than making such a pressure determination only at the diastolic and systolic points of the cardiac cycle, exciter waveform velocity is measured many times during a cardiac cycle (typically 50–200 times per second) and the resultant determinations of pressure are used to construct the output time varying blood pressure waveform. This process is described below with reference to FIG. 10.

In this embodiment, the natural blood pressure waveform is not scaled. Therefore, there is no need to separate the data into pulse segments as in step 704 of FIG. 6. This feature greatly simplifies the computational task. An additional advantage of this technique is that all of the information used in the analysis process is encoded in the exciter waveform, which is typically at a high frequency compared with that of both the natural blood pressure waveform and that of any artifact signals introduced by patient motion or respiration. Since all of these lower frequency signals can be removed by electronic filtering, this technique is extremely immune to motion induced artifact and similar sources of interference that might otherwise introduce errors into the measurement.

With the exception of this step, the initial processing steps 702, 706, 731 and 730 are substantially similar to those of previously described embodiments. The amplitude and phase of the exciter waveform determined in step 731 are continuous functions of time. The exciter waveform phase is converted to exciter waveform velocity as described previously, which is also a continuous function of time.

Using a relationship between pressure and velocity, determined during or subsequent to the initial calibration and periodically redetermined, the time dependent velocity function Vel(t) is readily transformed to a time dependent pressure function P(t). This transformation is represented by step 802. In a typical case, the pressure-velocity relationship might be as follows:

$$Vel(t)=a+bP(t) \qquad (10)$$

where the constants a and b were determined during step 750. In that case the velocity equation (10) can be used to perform the transformation of step 802.

Following a variety of checking steps, described below, that ensure the transformation used in 802 was correct, the minimum and maximum points of P(t) are determined for each cardiac cycle and displayed as $P_D(pred)$ and $P_S(pred)$ in step 805. Then, in step 806, the entire time dependent waveform is displayed as waveform 102.

DETERMINATION OF THE PRESSURE-VELOCITY RELATIONSHIP

In each of the embodiments described thus far, an important step involves the conversion of a measured phase to a deduced exciter waveform velocity, and conversion of that value to a pressure. In the case of the flow chart of FIG. 6, this process is integral to the calculation of the DC offset pressure $P_{D0}$. In the case of the embodiment described in FIG. 9, this process is integral to determination of $P_S$ and $P_D$. In the case of the embodiment described in FIG. 10, the process is integral to the determination of pressure at each point in time for which an output value is to be displayed as part of a "continuous" pressure waveform display.

The relationship between pressure and velocity is dependent on many factors including the elastic properties of the artery along which the exciter waveform travels. This relationship varies considerably between patients, and must therefore be determined on a patient by patient basis, although a starting relationship derived from a pool of patients can be used. This determination occurs during step 750 in each of the embodiments described in FIGS. 6, 9, and 10, and the relationship is stored in the processor in either a tabular form, or as an analytical relationship. In step 734 in FIGS. 6, 9 and 10, a variety of parameters are examined to determine whether the system calibration continues to be acceptable. As part of that process, it is determined whether the existing pressure-velocity relationship continues to be valid. If not, a recalibration can be initiated.

In most patients there is a monotonically increasing relationship between velocity of propagation of the induced perturbative pressure excitation along the arterial system and pressure. Over a certain range this relationship can be approximated as linear. In some cases a more complicated functional relationship between pressure and velocity may need to be used. In general the relationship can be well described by an equation of order 1 or 2 and the collection of a series of (pressure, velocity) value pairs and the use of a fitting process allows the determination of an appropriate relationship between pressure and velocity. In some cases, use of a predetermined general relationship with coefficients dependent on patient parameters such as weight, height, heart rate or age is possible.

One technique for pressure-velocity relation determination involves determination of pressure at diastolic, mean and systolic points at the substantially simultaneous time that velocity measurements are made at the same three points in the cardiac cycle. These three pairs of points can then be fit to determine a pressure-velocity relationship.

In one embodiment of the pressure-velocity relationship determination process, an occlusive cuff measurement is made on the contralateral arm (opposite arm) to that upon which the perturbation and detection process are occurring. It is then possible to perform a conventional cuff based measurement of blood pressure in one arm, yielding measurement of mean, systolic and diastolic pressures, substantially simultaneously with measurements of mean, systolic and diastolic velocities in the opposite arm. So long as it has been ascertained in advance that the patient has substantially similar pressures in both arms and that the two arms are either maintained at constant heights or correction is made for hydrostatic pressure differences between limbs, then it is valid to use the pressure in one arm as a proxy for pressure in the other. In this way it is possible to obtain three pairs of pressure and velocity measurements taken during a single time interval. A curve fitting process can be used to determine a pressure-velocity relationship that best describes this data and that relationship can be used as the basis for future prediction of pressure from measured velocity. In general it has been found that the use of a linear pressure-velocity relationship, such as in the velocity equation (10) outlined above, yields good results. In that case the fitting process yields values for the coefficients a and b.

In an alternative embodiment the cuff measurement and velocity detection and perturbation can all be made on a common limb, such as a single arm. Since the process of making a cuff measurement involves occlusion of the limb, measurements of perturbation velocity during cuff pressurization yield results different to those in an unperturbed limb. In one embodiment, measurements of velocity would be made before or after cuff inflation and the measured velocities and pressures would thus be somewhat offset in time. In a patient with stable blood pressure this may not introduce significant errors, although a typical cuff inflation time of 30–45 seconds implies time offsets of that order of magnitude between the velocity and pressure measurements. In cases where this time offset introduces unacceptable errors, the determination technique can be modified to introduce some averaging or trending. As an example, alternating velocity and cuff blood pressure measurements could be made over a period of minutes and the results could be averaged to reduce errors due to blood pressure fluctuation with time. Other forms of time series manipulation familiar to one skilled in the art could be used to develop a valid relationship between blood pressure and exciter waveform velocity using the pairs of velocity and pressure measurements obtained by this technique.

In a further embodiment of the pressure-velocity relationship determination process, an advantage can be taken of the fact that measurement of blood pressure by an occlusive cuff measurement involves a controlled and known modification of the transmural pressure in the artery. In this embodiment, depicted in FIG. 12, an occlusive cuff 811 is placed over the exciter 202 and noninvasive sensor 210. The occlusive cuff 811 can also serve the function of cuff 110 in FIG. 1. The pressure in cuff 811 is controlled via tube 812 connected to processor 100. The exciter 202 and sensor 210 separation and cuff size are chosen so that the exciter 202, the detector 210 and the portion of the limb between them are all covered by the cuff 811.

As the pressure in the cuff 811 is increased, the transmural pressure in the artery is decreased by a known amount. Thus, during the period of cuff 811 inflation and deflation a variety of transmural pressures are experienced in the artery and a variety of velocities will be observed. Since the cuff 811 pressure is known at all times, and the end point of the cuff measurement is measurement of systolic, diastolic and mean pressure measurement, it is possible after the measurement to reconstruct the value of transmural pressure at each point in time during the occlusive cuff measurement. This time series of varying transmural pressures can then be regressed against the time series of velocities measured over the same time interval to produce a sophisticated and highly accurate determination of the velocity pressure relationship over a range of transmural pressures from zero to systolic pressure. Increased accuracy and robustness and insensitivity to patient temporal pressure fluctuation can clearly be obtained by repetition of this determination and use of averaging or other time series processing to minimize errors due to measurement inaccuracy and to patient pressure fluctuation.

While the velocity equation (10) is commonly adequate, in some instances more complex functions are appropriate to describe the pressure-velocity relationship and functional forms such as quadratic, cubic or other more complex analytical functions can be used. In such cases the following improvement to the above embodiments can be important.

In each of the pressure-velocity determination embodiments described above, only the pressure values of mean, systolic and diastolic pressure are measured. The following improvement can be applied to each of them. The noninvasive sensor signal is filtered to provide an output representative of the naturally occurring blood pressure pulse as a function of time during a given cardiac cycle. Similarly, the velocity of the exciter waveform is determined as a function of time during a given cardiac cycle. By using the values of mean and diastolic and systolic pressure determined by the calibration (e.g. occlusive cuff) measurement to scale a naturally occurring blood pressure waveform measured contemporaneously with the cuff measurement by the noninvasive sensor, a calibrated pressure waveform is determined for the blood pressure. While sensor movement and a variety of other phenomena limit the use of this calibrated waveform to a relatively short period of time, it can be used during any of the pressure-velocity relationship determination procedures described above to yield many pressure-velocity measurement pairs during a single cardiac cycle. The use of these extra points may improve the accuracy of the relationship determination, particularly in circumstances where the relationship functionality is more complex than can be described by a linear relationship, such as a nonlinear relationship.

In each of the embodiments described above, an occlusive cuff is used to occlude blood flow in an artery of the patient. Other occlusive devices such as bladders, bands, pressurized plates or diaphragms can be used with equal effect.

In each of the embodiments described above, determination of the pressure-velocity relationship is made from a series of pressure-velocity pair measurements made over a range of pressures. In general, it is possible to extrapolate this relationship outside the range of the measurements used in the determination. The range over which such extrapolation is valid is determined based on examination of data from a study of multiple patients, and is related to the form of the pressure-velocity relationship and the values of its coefficients. The decision process embodied in step 734 in FIGS. 6, 9 and 10, includes an analysis of whether such extrapolation can be extended from the regime of initial calibration to that of the presently measured velocity. If not, the calibration process of step 750 is initiated and the determination process described in this section is repeated.

A variety of other factors are considered in making the determination as to whether a recalibration, step 750, is required. These factors include examination of the amplitude and phase of the exciter waveform and an examination of their dependence on frequency, detector-exciter separation, and on various other factors including each other.

REDETERMINATION OF THE PRESSURE-VELOCITY RELATIONSHIP

Subsequent to the initial determination of the pressure-velocity relationship described above, it is desirable to periodically determine whether that relationship is still applicable. The relationship may become less applicable with time because of physiological changes in the patient due to endogenous or exogenous chemicals in the body that can affect the arterial muscular tone and, thus, the velocity of propagation of the exciter waveform. Even in the absence of changes in the patient, imperfect determination of the relationship due to measurement errors may lead to the need to check or redetermine the relationship periodically during a monitoring procedure.

The determination procedures described above involve the use of an occlusive cuff. While these determination procedures can be repeated periodically, there is a limit to the frequency of such measurements due to the fact that each measurement results in a period on the order of a minute in which the circulation of the limb is impaired. Furthermore, occlusive cuff measurement is uncomfortable and therefore it is desirable to minimize its use. Accordingly it is desirable for there to be a technique of redetermining the velocity pressure relationship which does not involve a conventional occlusive cuff measurement and which is relatively comfortable and pain free, which is rapid compared to an occlusive cuff measurement and which can be repeated frequently.

Figure 10B:
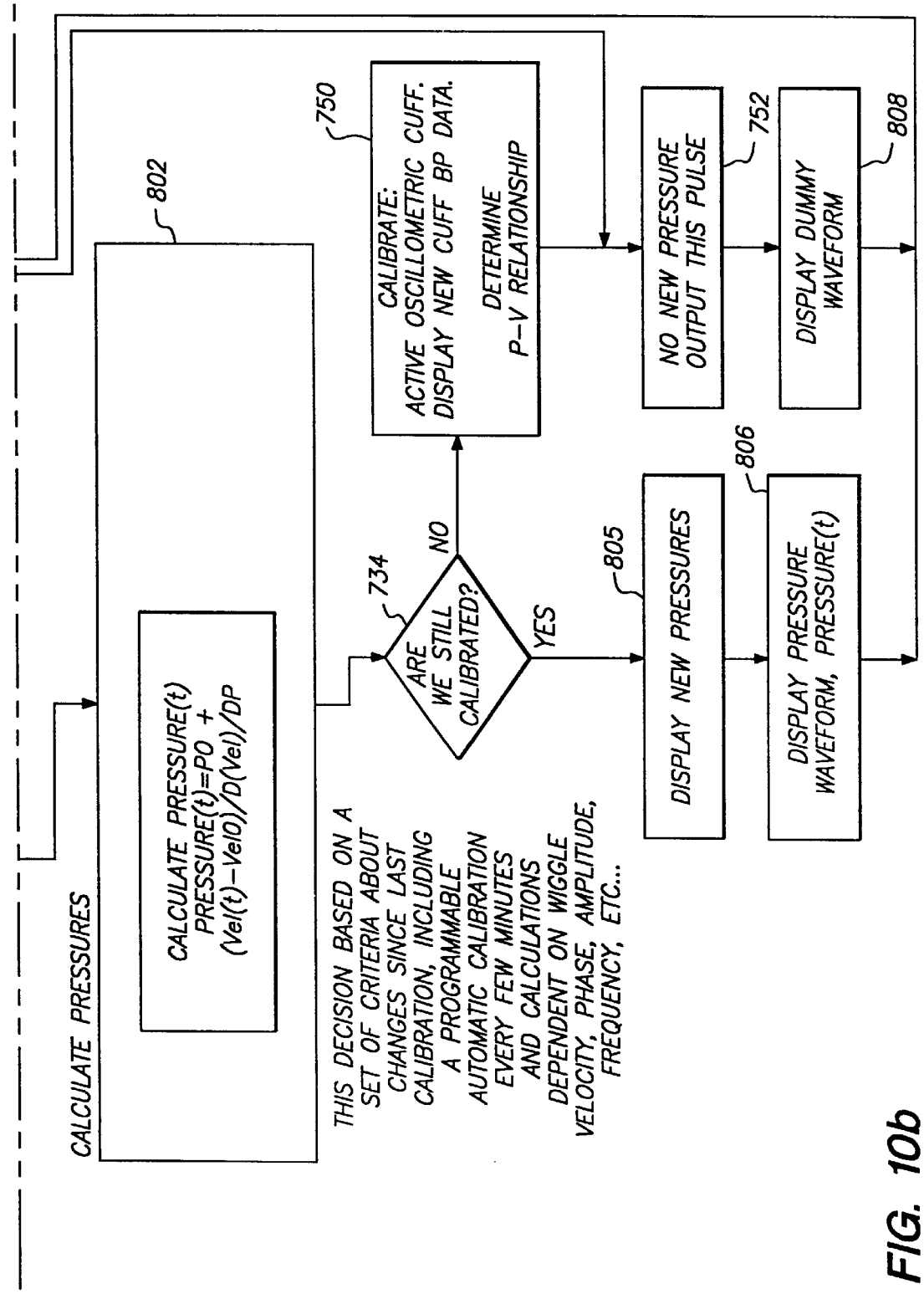

In FIGS. 9 and 10, this process is represented by step 901 in which the pressure-velocity relationship is periodically redetermined. The interval of such redetermination is affected by the frequency of expected changes in the relationship. This is expected to be relatively slow on the scale of the cardiac cycle and should probably be chosen to be long with respect to the respiratory cycle to avoid interference. Time constants of the order of $\tau=30$ seconds or more are suitable, but other time constants may also be appropriate. Subsequent to each redetermination, the previously determined historical relationship is compared with the new relationship in step 902. If the relationship has changed significantly, the relationship used in the determination of pressure is updated in step 903. As part of this process, averaging of the variously redetermined historical relationships or other time series analysis may be used to provide increasingly accurate relationships for use as the time elapsed since the initial calibration increases.

In the embodiment of redetermination described here, a relationship of the type of the velocity equation (10) is assumed. This technique can be generalized to other functional forms of the relationship. In the functional form of the velocity equation (10), it is necessary to determine the constants a and b corresponding to the offset and slope respectively, of the relationship. In this embodiment, two separate operations are used to determine the two coefficients a and b.

Figure 12:
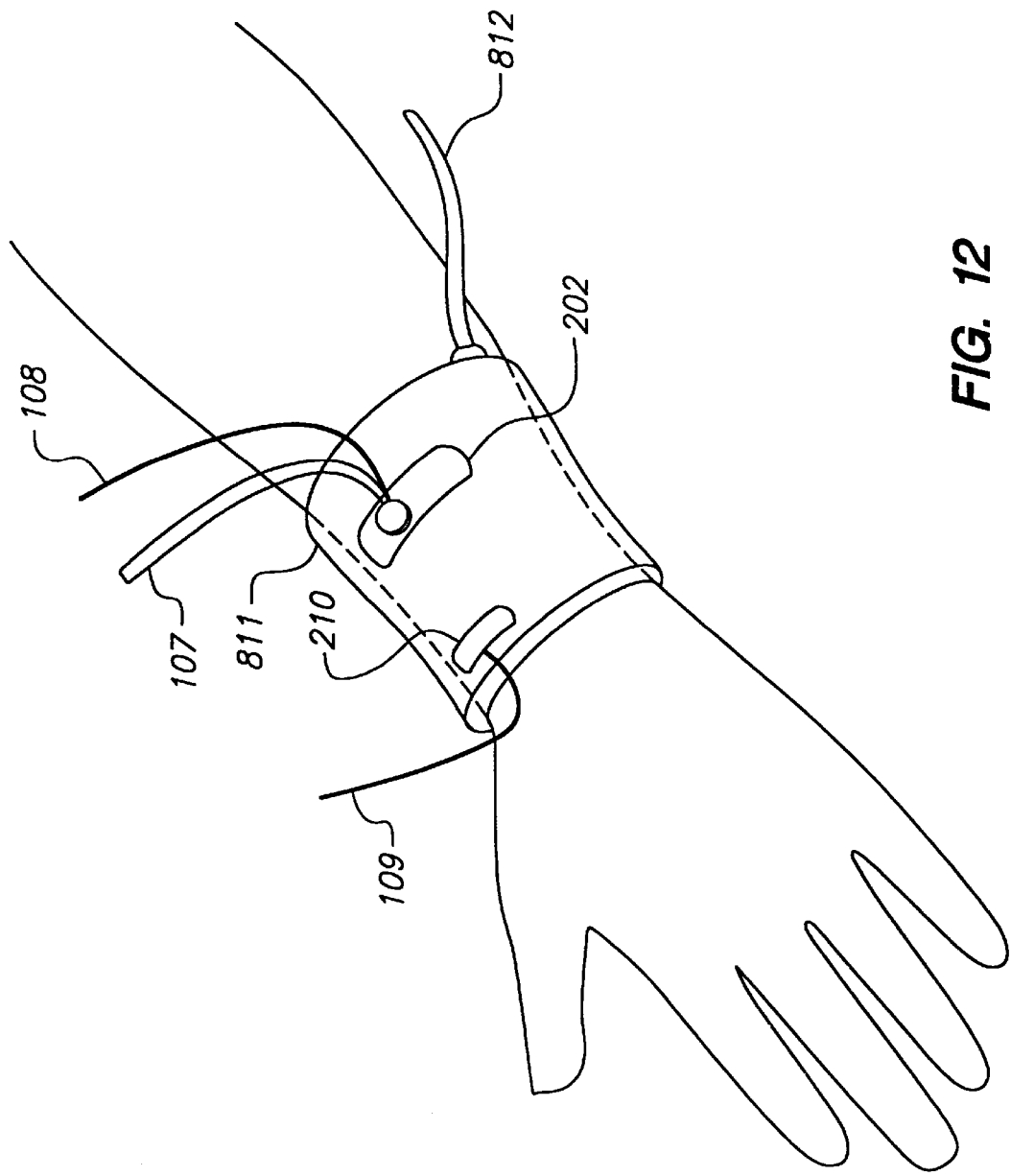
FIG. 12 depicts a pressure redetermination apparatus according to an embodiment of the invention.

To determine the relationship slope b, the embodiment depicted in FIG. 12 is used. The pressure in cuff 811 is varied in accordance with a time dependent pressure function $\delta P(t)$. The function $\delta P(t)$ typically has the form of a square wave of amplitude 10 mm Hg, period 30–60 seconds, and mean pressure of 5 mm Hg. However, alternate functional forms such as sinusoids, triangular waves and other shapes can also be used, and larger and smaller amplitudes and offset pressures can also be used. In the example described here, the artery is subject to alternating pressures of 0 mm Hg and of 10 mm Hg. For constant diastolic and systolic pressures, the transmural pressures at the diastolic and systolic points, thus, alternate between $(P_D, P_S)$ and $(P_D-10, P_S-10)$. The corresponding measured velocities are therefore $(Vel(P_D), Vel(P_S))$, and $(Vel(P_D-10), Vel(P_S-10))$. The coefficient b can be determined using the formula:

$$b=(Vel(P_S)-Vel(P_S-10))/10=(Vel(P_D)-Vel(P_D-10))/10 \qquad (11)$$

Clearly, averaging over longer periods than the time constant of a single period of $\delta P(t)$ leads to increased accuracy of this measurement.

In one embodiment, the above technique for redetermination can be used alone as a determinant of the need for the calibration step of step 750 in FIGS. 6, 9 and 10 to be repeated. In an alternative embodiment, continual updating of the value of b allows continual determination of the value of pressure without the need for a recalibration. As an illustration, the equation:

$$P_D(Pred)=P_{D0}+(Vel_D-Vel_{D0})/b \qquad (12)$$

can be used at any time to predict diastolic pressure if the value of b has remained unchanged since the initial calibration. In the case that a is relatively constant, and that b has changed but has been continuously monitored, the prior equation can be replaced by the equation:

$$P_D(\text{pred}) = P_{D0} + \int \left[ \frac{d}{dt} \left[ [Vel_D(t) - a]/b(t) \right] \right] dt \qquad (13)$$

In a further embodiment of the recalibration process, the coefficient a can also be periodically redetermined. There are a number of ways to determine the offset a. In a preferred embodiment, the cuff 811 in FIG. 12, is rapidly inflated to a pressure between the diastolic and systolic pressures of the last few pulses. At the time in the cardiac cycle in which cuff pressure equals or is within some determinable increment of intraarterial pressure, the artery will close or reopen depending on the phase of the cardiac cycle. Many signatures can be observed of this arterial closing or opening. These include Korotkoff sounds, wall motion, arterial volume monitoring, plethysmography, blood flow and electrical impedance.

The time in the cardiac cycle at which a signature appears can then be correlated with the cuff pressure in cuff 811, and the waveshape of the velocity pulses of nearby cardiac cycles can be used to associate a single velocity with a single pressure (Vel1, P1). From this pair, the value of coefficient a can be calculated using the formula Vel1=a+bP1. While this measurement of coefficient a involves application of a moderate pressure to cuff 811, the pressure is less than the occlusive pressure associated with a conventional blood pressure cuff measurement. Furthermore, the pressure need only be applied for the duration of one or at most several cardiac cycles. This is in contrast to a conventional cuff measurement in which the cuff must be fully or partially inflated over a significant number of cycles, typically of the order of 30–60 seconds. This instantaneous single value measurement can thus be made more rapidly and less traumatically than a multi-valued conventional occlusive cuff pressure measurement.

MULTIPLE PERTURBATIONS

For each of the different embodiments described hereto, an additional embodiment is described using multiple perturbation waveforms. All the features and advantages of the prior embodiments are applicable to these embodiments.

In the case of each of the previously described embodiments an embodiment is described in which the apparatus further induces a second exciter waveform into the arterial blood. An example second exciter waveform is one that has a frequency different from that of the first exciter waveform. It is noted that although the discussion of the second embodiment concentrates on a second exciter wave, any number of two or more exciter waves can be used to determine the perturbation velocity measurement.

In operation, processor 100 generates two exciter waveforms and communicates the waveforms to the exciter 202 via air tube 107. The exciter 202 responds by inducing both exciter waveforms into the patient. Noninvasive sensor 210 generates a signal responsive to a hemoparameter and transmits the signal to the processor 100 via wire 109.

The processor filters the noninvasive sensor signal into components of the natural waveform, a first exciter waveform, a second exciter waveform and noise. The processor determine the phase relationship of the first exciter waveform to a first reference input and determines the phase relationship of the second exciter waveform to a second reference input.

Once the processor has determined the phase of the exciter waveforms, the processor then generates a plurality of points, the slope of which relates to the velocity of the exciter waveform. This is shown in FIG. 8c, where the slope of the line is $2\pi d/\text{Vel}$, and where d is distance and Vel is velocity. Since the distance is fixed and the slope is related to blood pressure, and since the slope changes based on changes in blood pressure, the velocity of the exciter waveform is determined.

The technique described above yields a measurement of the group velocity. In contrast, the techniques described in previous embodiments result in the measurement of a phase velocity or of a pseudo-phase velocity in the case that the value of n of the phase equation (7) can not be uniquely determined. In a dispersive system these values need not always agree. However, phase, group and pseudo-velocity are monotonically varying functions of pressure. Thus, a measurement of any one of the three is a basis for a pressure prediction, so long as the appropriate pressure-velocity relationship is used.

An additional benefit of the use of multiple frequency perturbations is that it allows the unique determination of the value of n in the phase measurement equation described above. The unique determination of the value of n is also called resolving the cycle-number ambiguity. This allows the use of actual phase velocity, rather than of the pseudo-velocity described earlier in the multi-perturbation analogues of the embodiments depicted in FIGS. 6, 9 and 10.

Once the velocity is determined, a prediction of blood pressure is made according to FIG. 8a, showing the relationship of velocity to pressure. Thus, it is possible to determine the blood pressure with few, or zero, calibrations.

Figure 11:
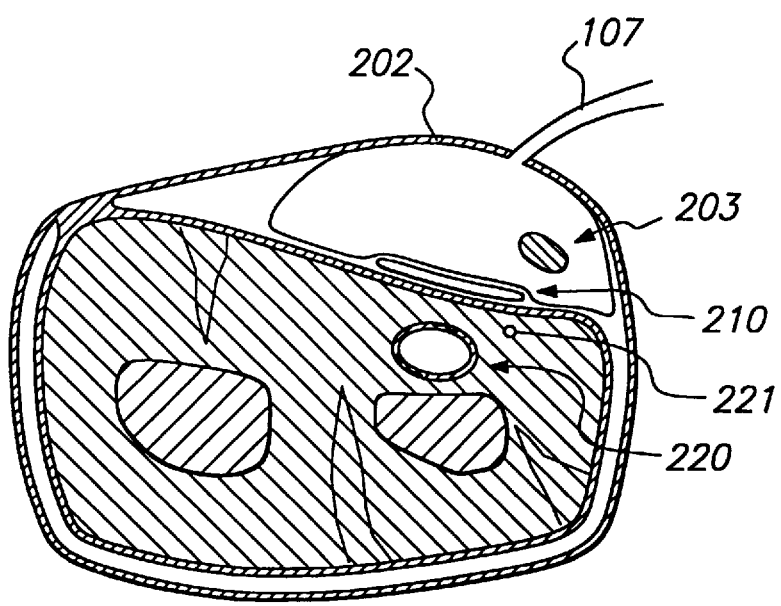
FIG. 11 depicts an exciter and noninvasive sensor attached to a patient.

Another embodiment is depicted in FIG. 11 showing a cross section of an exciter 202 and noninvasive sensor 210 at the same position above the blood vessel 220. The proximate location of the exciter and the sensor permits measurement of the blood vessel's response to the perturbations. In this embodiment, the noninvasive sensor is responsive to a hemoparameter such as blood flow or blood volume. These parameters can be measured with a sensor such as a photoplethysmograph. Detected changes in the blood vessel due to the natural pulsatile pressure are calibrated using external exciter pressure oscillations and compared against the sensor signal by the processor.

DETERMINATION OF THE PATIENT'S PHYSICAL CONDITION

A. In the parent patent applications of Caro et al, and discussed above, techniques are described for the measurement of physiological parameters such as blood pressure, arterial elasticity, cardiac output, and other parameters. As part of those techniques, a procedure is described to determine a relationship between a patient's blood pressure P and the velocity of propagation Vel of an induced high frequency pressure perturbation along the artery. This relationship can have various forms and can be described generally as:

$$Vel = f(P) \quad (14)$$

where f(P) is a function of pressure. An important step in the Caro techniques is the determination of the nature of the function f over a range of pressure in a given patient. In the Caro techniques, the relationship of equation (14) was used to determine pressure following a measurement of velocity Vel. In the present embodiments, we describe the use of the information contained in the form of the function f to determine information relating to the physical condition of the arterial system.

In this context, we define several terms. As described, the propagation of the exciter waveform is a function of several factors. The waveform propagation is a function of the blood pressure in the artery and a function of the artery's mechanical properties. For example, as the blood pressure increases the velocity increases, and stiffer arteries also tend to be associated with increased velocity. Therefore, as used herein propagation parameters include parameters such as velocity, pseudo-velocity, amplitude and attenuation and their respective components such as offset and slope. The general mechanical factors that influence propagation of the exciter waveform are defined as mechanical properties such as arterial compliance, arterial distensibility and arterial elasticity.

The information regarding the physical condition of the arterial system can then be used to generate an output that can be used by health care personnel in the diagnosis and management of diseases such as cardiovascular disease.

B. In the previously referenced patent applications by Caro et al, and discussed above, there is described an invention capable of determining the relationship between the velocity of propagation of a pressure wave in a human arterial segment and the pressure in that segment. In the formalism of this application, the previously discussed invention describes a technique for noninvasively determining the nature of the relationship described by equation (14) and of determining the nature and detailed description of the function f(P).

Now from theoretical considerations, we expect that the velocity of propagation of a pressure wave in the arterial system can be modeled by the Moens-Korteweg equation (Moens, A.I.: Die Pulskurve. Leiden: E.J. Brill.; 1878.):

$$Vel=[(Eh)/(2\rho r)]^{1/2} \tag{15}$$

or by the Bramwell-Hill equation (Bramwell, J. C., and Hill, A. V.: Proc. R. Soc. Lond. [Biol.]:93:298, (1922).), which is substantially identical for the case of a thin-walled tube:

$$Vel=[r/(2\rho(dr/dP))]^{1/2}[1/(2\rho D)]^{1/2} \tag{16}$$

where r is the vessel radius, ρ is the blood density, E is the elastic modulus of the artery wall, h is the wall thickness, (dr/dP) is the vessel compliance, D is the vessel distensibility, and P is the arterial pressure. Thus by comparing the experimentally determined function f(P) of equation (14) with the equations of (15) and (16), information can be obtained about the physical properties of the arterial system E, r, h, D and ρ and their dependence on pressure.

Equations 15 and 16 are relatively simple relationships and are provided as examples. More complex and more accurate relationships can be developed by theory or by experiment and may include models using neural networks and patient data. Additionally, some more complex relationships have been reported in the literature and are known by those skilled in the art. R. Holenstein, *A Viscoelastic Model for use in Predicting Arterial Pulse Waves*, J. Biom. Eng., vol. 102, p. 318 (1980). The discussion that follows can clearly be generalized to include both relatively simple models and more complex models.

Figure 13:
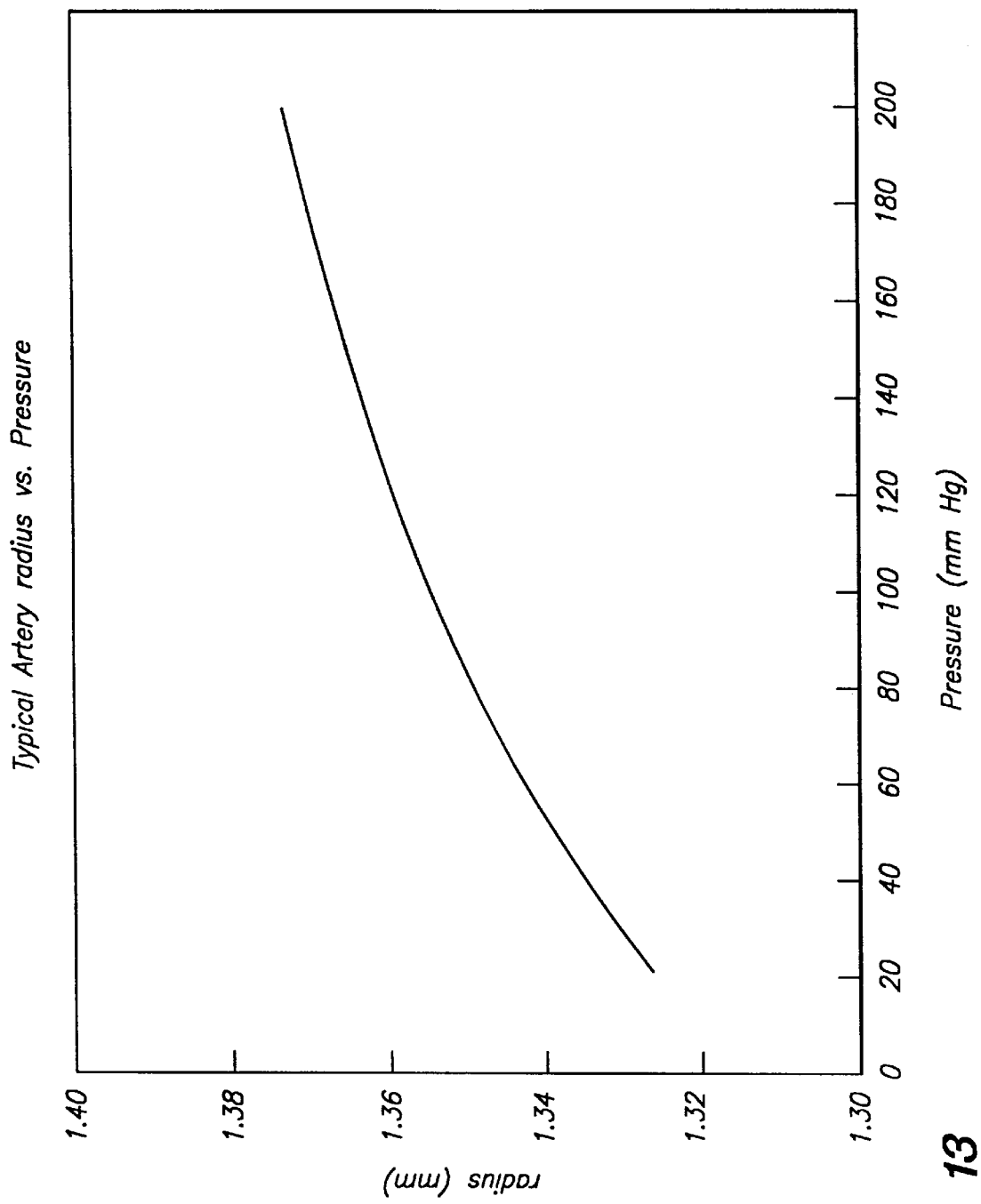
FIG. 13 is a graphical illustration showing the relationship between typical artery radius and pressure.

Most human arteries demonstrate a nonlinear relationship between radius and pressure. A typical radius vs. pressure curve for the radial artery will be similar to that shown in FIG. 13, where we have plotted an equation which has been successfully used to model radius vs. pressure data from in vivo experiments on the radial artery. Y. Tardy, *Non-invasive Estimate of the Mechanical Properties of Peripheral Arteries from Ultrasonic and Photoplethsmographic Measurements*, Clin. Phys. Physiol. Meas., vol. 12, no. 1, p. 39 (1991).

Figure 14:
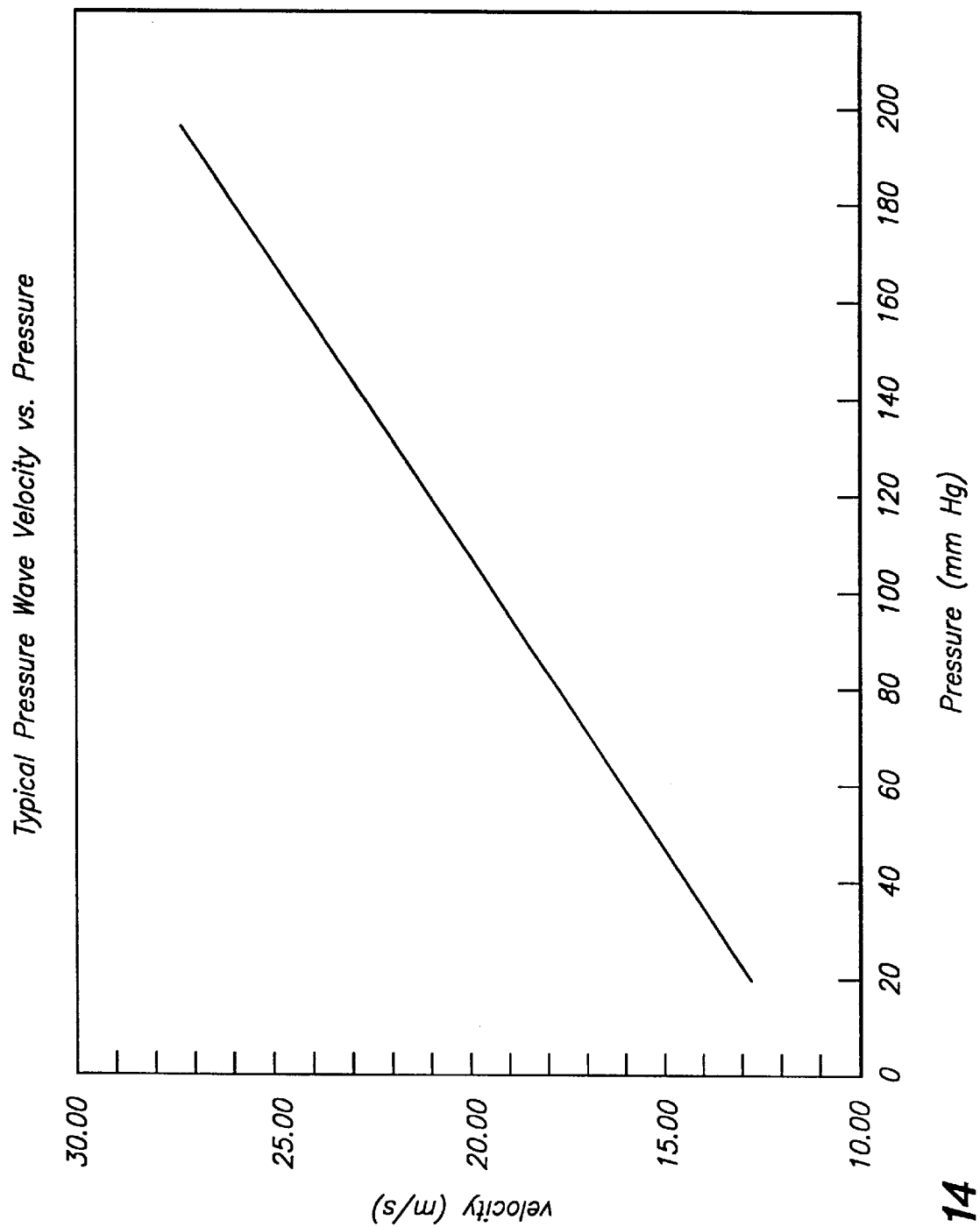
FIG. 14 is a graphical illustration showing a typical exciter waveform velocity versus blood pressure.

Because the arterial compliance (dr/dP) decreases monotonically with increasing arterial pressure, the pressure wave velocity increases monotonically with increasing arterial pressure. See, for example, J. Pruett, *Measurement of Pulse-Wave Velocity Using a Beat-Sampling Technique*, Annals Biomed. Eng., vol. 16, p. 341 (1988); and M. Landowne, *A Method Using Induced Waves to Study Pressure Propagation in Human Arteries*, Circulation Res., vol. 5, p. 594 (1957). This relationship is shown in FIG. 14.

C. Determine Arterial Distensibility

In one embodiment, the apparatus of the previously described inventions, discussed above, is used to determine the relationship of equation (14) and the function f(P). A value for the arterial distensibility, D(P), as a function of pressure is then determined from the equation:

$$D(P)=1/[2\rho(f(P))^2] \tag{17}$$

where the value of ρ is either measured for that patient, or is generally assumed to be relatively invariant from patient to patient and equal to a value determined from an average over a pool of patients. For many purposes it may be adequate to assume that the value of ρ is that of water, or ρ=1, since the primary constituent of blood is water.

The values of distensibility as a function of pressure are then stored in memory and displayed for the use of health care personnel in diagnosis or treatment of the patients disease.

D. Determine Arterial Compliance

In another embodiment, the method and apparatus of the previous embodiment are combined with a device which has the capability of making a measurement of the arterial radius r. An example of such a device could be an ultrasound imaging device or other ultrasound "pulse ranging" device in which a pulse of ultrasound is directed at an angle across the artery and a reflection is detected from both walls of the artery. By combining knowledge of the speeds of sound in tissue and blood with information concerning the angle with which the direction of propagation of the ultrasound beam intersects the arterial axis, a measurement of the time elapsed between detection of the reflections from each of the arterial walls can be analyzed to provide a measurement of arterial diameter.

Techniques for determining arterial diameters, such as that described above, have been widely described in the scientific literature. Examples of techniques for measuring arterial diameters are described in J. Meister, *Non-invasive Method for the Assessment of Non-linear Elastic Properties and Stress in Forearm Arteries in Vivo*, J. Hypertension, vol. 10 (supp 6), p. 523 (1992); J. Levenson, *Pulsed Doppler: Determination of Diameter, Blood Flow, Velocity, and Volume Flow of Brachial Artery in Man*, Cardiovascular Res., vol. 15, p. 164 (1981); and Y. Tardy, *Non-invasive Estimate of the Mechanical Properties of Peripheral Arteries from Ultrasonic and Photoplethsmogaphic Measurements*, Clin. Phys. Physiol. Meas., vol. 12, no. 1, p. 39 (1991).

Other means for determining arterial diameter can include x-ray measurement following injection of contrast media into the circulatory system, the use of Magnetic Resonance Imaging techniques, or the manual entry into the device of values measured by a separate machine.

Following determination of the value of radius r, the arterial compliance C(P) or dr/dP can be determined according to the formula:

$$C(P)=dr/dP=rD \tag{18}$$

F. In each of the above mechanical property determinations, we have described determination of a property as a function of blood pressure. In a simplified embodiment, the mechanical property can be determined at a single blood pressure, such as the resting blood pressure of the patient. For this embodiment, equation 17 becomes:

$$D=1/[2\rho(Vel)^2] \tag{20}$$

for the distensibility, D, at a specific pressure for which the velocity of propagation is Vel. In such an embodiment, no calibration or determination of the relationship between velocity and pressure is required. Instead, health care decisions are made simply on the basis of the magnitude of the velocity in a patient at rest, or of one of the derived mechanical properties such as arterial compliance, distensibility or elasticity.

In a refinement of this embodiment, the patient's blood pressure is measured and the value of the mechanical property or the velocity is compared with a previously stored value. The previously stored value can be, for example, that of the patient stored from his last visit, or that of a population of patients.

The resulting arterial compliance can then be displayed in display 120 of FIG. 1.

E. Determine Arterial Elasticity

In another embodiment, the arterial wall thickness h can be determined either by a separate apparatus or by a subsystem incorporated within the above described apparatus. An example of a technique for making this measurement is described in the work of Y. Tardy, *Non-invasive Estimate of the Mechanical Properties of Peripheral Arteries from Ultrasonic and Photoplethsmographic Measurements,* Clin. Phys. Physiol. Meas., vol. 12, no. 1, p. 39 (1991); and Y. Tardy, *Dynamic Non-invasive Measurements of Arterial Diameter and Wall Thickness,* J. Hypertension, vol. 10 (supp 6), p. 105 (1992).

Following determination of r and h, the arterial elastic modulus E can be determined from the equation $$E(P)=[2\rho r(f(P))^2]/h \qquad (19)$$

Note that arterial thickness is a property that changes slowly over a lengthy period of time, such as years, due to biological changes in the material of the arteries. This is in contrast to E and r which can change over periods as short as minutes in response to endogenous or exogenous chemical stimulus.

Therefore in situations where a drug regimen is being optimized using E as the parameter to be maximized or otherwise affected, where time sequences of measurements of arterial elasticity need to be made in a given patient, measurement of relative elasticity may be adequate. In this case, no specific measurement need be made of absolute wall thickness.

A variety of derived parameters such as arterial wall stress or strain can be determined following the determination of the underlying physical properties of the artery. These parameters provide useful information for health care personnel. In the case where relative measurements only are required in a given patient, the parameter Q=(Eh) might profitably be used.

F. In each of the above mechanical property determinations, we have described determination of a property as a function of blood pressure. In a simplified embodiment, the mechanical property can be determined at a single blood pressure, such as the resting blood pressure of the patient. For this embodiment, equation 17 becomes:

$$D=1/[2\rho(Vel)^2] \qquad (20)$$

for the distensibility, D, at a specific pressure for which the velocity of propagation is Vel. In such an embodiment, no calibration or determination of the relationship between velocity and pressure is required. Instead, health care decisions are made simply on the basis of the magnitude of the velocity in a patient at rest, or of one of the derived mechanical properties such as arterial compliance, distensibility or elasticity.

In a refinement of this embodiment, the patient's blood pressure is measured and the value of the mechanical property or the velocity is compared with a previously stored value. The previously stored value can be, for example, that of the patient stored from his last visit, or that of a population of patients.

G. Other Derived Parameters

In another embodiment, the derivative of velocity with respect to pressure, dv/dp, can be determined from the measured relationship between velocity and pressure. Also, the derivative of amplitude with respect to pressure and attenuation with respect to pressure can be determined. This, and other higher order derivatives of the function f(P) can be expected to show a dependence of both magnitude and form on aging and on degree of cardiovascular disease.

H. Additional Embodiments to Determine A Physical Condition

In a refinement of each of the above embodiments, information is stored in the memory of the processor performing the determination of the various arterial properties from the measured function f(P). The determined physical properties are then compared with that stored information and 'information about the state of health of the patient is derived from a comparison of the measured values of physical properties of the artery and the stored information. As an example, it is likely that excessively stiffened arteries are symptomatic of underlying cardiovascular disease.

In one example, the processor contains information concerning the arterial distensibility or compliance or elastic modulus as a function of age, weight and other patient characteristics. This information would be in the form of average values of these properties for "healthy" and "diseased" patients, together with the standard deviations of the distributions of values of these parameters determined from a study of a cross section of the population.

By comparison of the measured values of, say, elastic modulus with the stored data from the patient population studied, a determination could be made of the probability that the patient was "healthy" or "diseased" and this information could be displayed for use by health care personnel.

In a preferred technique, the measurements described in the embodiments are performed at a variety of anatomical sites. Placement of the device over the radial artery and measurement of radial artery properties has advantages of anatomical convenience. However, numerous other sites can be used and similar measurements can be performed in the brachial, carotid, tibial, illiac and femoral arteries as common examples. Venous measurements can also be performed and may be useful to determine, for example, the return blood flow to the heart and any problems that the blood is having in returning to the heart.

In each of the above embodiments, the velocity of propagation of the pressure perturbation is measured and various arterial physical properties are derived therefrom. In addition, it is often possible to measure the attenuation of the propagating perturbation in the artery. This measurement can be conveniently made by making use of information contained in the received exciter waveform signal at several separate frequencies or distances.

The attenuation coefficient of propagation also is dependent on a variety of important physical properties of the artery. Thus, measurement of the attenuation coefficient will allow the deduction of the values of various additional arterial properties. As an example, the attenuation in the artery is a function of wall viscosity and can be described by a variety of simple models such as those in M. Anliker, *Dispersion and Attenuation of Small Artificial Pressure Waves in the Canine Aorta,* Circulation Res., vol. 23, p. 539 (October 1968). Measurement of attenuation may thus yield the derived quantity of wall viscosity of the arterial segment under consideration. The frequency dependence of attenuation can also be measured and is also clinically useful.

I. Clinical Research to Support Utility of the Embodiments

The embodiment depicted in FIG. 1 was used to continuously monitor the propagation velocity of a pressure perturbation in the 100–200 Hz range in the radial artery. A transmitted exciter waveform (excitation signal) was delivered to the radial artery just distal to the elbow by the exciter 202 (pneumatic bladder). A noninvasive sensor 210 (piezoelectric transducer) was placed over the radial artery proximal to the wrist to detect both the received exciter waveform (propagated signal) and the physiological waveform (arterial pulse). Arterial pressure was measured simultaneously in the contralateral arm by an arterial catheter. The transmitted exciter waveform, received exciter waveform, and arterial blood pressure were continuously sampled and stored by a computer for analysis. The velocity of the exciter waveform was determined from the propagation distance and the difference in phase between the transmitted exciter waveform and the received exciter waveform.

The continuous nature of a single frequency sinusoidal excitation signal prevents a unique determination of the total propagation phase, because the number of wavelengths between the exciter position and the sensor position is unknown. In this clinical study information from multiple frequencies was used, together with the assumption that the variation of velocity with frequency is small, to determine the total phase and, hence, the velocity. This assumption is supported by M. Anliker, *Dispersion and Attenuation of Small Artificial Pressure Waves in the Canine Aorta,* Circulation Res., vol. 23, p. 539 (October 1968).

Twenty patients undergoing major elective surgery requiring intraarterial blood pressure monitoring were studied. The results of this study was reported in R. Pearl et al., Anesth. 83,A481 (1995).

VARIATIONS ON THE DISCLOSED EMBODIMENTS

Additional embodiments include an embodiment in which two or more detectors are positioned along the artery at different distances from a single exciter, and an embodiment in which two or more exciters are positioned along the artery at different distances from one or more detectors. In each of these embodiments, the information obtained from each exciter detector pair can be analyzed independently. The multiply redundant measurements of pressure that result can be combined to provide a single pressure determination that may be both more accurate and more immune from noise, motion artifact and other potential error sources. Similar redundancy can be achieved in the embodiments that use multiple exciter waveforms' by analyzing the results at each frequency independently and combining the results to provide enhanced robustness.

In addition, any combination of more than two elements (e.g. two exciters and one detector, two detectors and one exciter, one exciter and three detectors) allows the value of n in the phase equation (7) to be uniquely determined so long as the spacing of two of the elements is sufficiently small to be less than a wavelength of the propagating perturbation. Since the possible range of perturbation wavelengths at a given pressure can be determined from a pool of patients, selection of the appropriate spacing is straightforward and can be incorporated into the geometrical design of the device.

CONCLUSION

A close relationship between physiological parameters and hemoparameters supplies valuable information used in the present invention. The perturbation of body tissue and sensing the perturbation also supplies valuable information used in the present invention. Although the preferred embodiment concentrates on blood pressure, the present invention can also be used to analyze and track other physiological parameters such as vascular wall compliance, changes in the strength of ventricular contractions, changes in vascular resistance, changes in fluid volume, changes in cardiac output, myocardial contractility and other related parameters.

Calibration signals for the present invention can be obtained from a variety of sources including a catheter, manual determination, or other similar method.

The DC offset for the physiological parameter waveform can be obtained in a variety of ways for use with the present invention.

The exciter of the preferred embodiment uses air, but any suitable fluid can be used. Moreover, various exciter techniques can be used for inducing an exciter waveform into the patient such as an acoustic exciter, an electromagnetic exciter and an electromechanical exciter (e.g. piezoelectric device).

Various noninvasive sensors have been developed for sensing hemoparameters. These sensor types include piezoelectric, piezoresistive, impedance plethysmograph, photoplethysmograph, various types of strain gages, air cuffs, tonometry, conductivity, resistivity and other devices. The present invention can use any sensor that provides a waveform related to the hemoparameter of interest.

Having disclosed exemplary embodiments and the best mode, modifications and variations may be made to the disclosed embodiments while remaining within the subject and spirit of the invention as defined by the following claims.

What is claimed is:

1. A monitor for use in determining a patient's physical condition, comprising:

an exciter adapted to be positioned over a blood vessel of the patient and configured to induce a transmitted exciter waveform into the patient;

a noninvasive sensor spaced apart from said exciter, adapted to be positioned over said blood vessel and configured to sense a hemoparameter and to generate a noninvasive sensor signal representative of said hemoparameter containing a component of a received exciter waveform; and a processor coupled to said noninvasive sensor and configured to receive said noninvasive sensor signal and to process said noninvasive sensor signal to determine a physical property of the patient in order to provide a condition signal related to said physical condition.

2. The monitor of claim 1, further comprising:

a device configured to provide a pressure signal representative of a blood pressure of the patient; and wherein said processor is configured to receive said pressure signal and to provide said pressure signal as an output.

3. The monitor of claim 2, wherein:

said processor is configured to compare said condition signal to a previously stored condition signal to provide a relative condition signal related to said physical condition.

4. The monitor of claim 1, further comprising:

a device configured to provide a pressure signal representative of a blood pressure of the patient; and wherein said processor is configured to receive said pressure signal and to process said pressure signal to provide said condition signal.

5. The monitor of claim 4, wherein:

said processor is configured to compare said condition signal to a previously stored condition signal to provide a relative condition signal related to said physical condition.

6. The monitor of claim 4, wherein:

said processor is configured to determine a propagation parameter of said received exciter waveform and to process said propagation parameter and said pressure signal to provide said condition signal.

7. The monitor of claim 6, wherein:

said processor is configured to determine a relationship between said propagation parameter and said pressure signal; and said processor is configured to provide said condition signal based at least in part on said relationship.

8. The monitor of claim 4, wherein:

said processor is configured to determine a derivative of a propagation parameter of said received exciter waveform and to process said derivative and said pressure signal to provide said condition signal.

9. The monitor of claim 8, wherein:

said processor is configured to compare said condition signal to a previously stored condition signal provide a relative condition signal related to said physical condition.

10. The monitor of claim 4, wherein:

said physical condition is a mechanical property of said blood vessel; and said processor is configured to process said noninvasive sensor signal and said pressure signal to provide said condition signal related to said mechanical property.

11. The monitor of claim 10, wherein:

said processor is configured to compare said condition signal to a previously stored condition signal provide a relative condition signal related to said physical condition.

12. The monitor of claim 1, wherein:

said processor is configured to compare said condition signal to a previously stored condition signal to provide a relative condition signal related to said physical condition.

13. The monitor of claim 1, wherein:

said processor is configured to determine a propagation parameter of said received exciter waveform and to process said propagation parameter to provide said condition signal.

14. The monitor of claim 1, wherein:

said processor is configured to store a relationship between a propagation parameter and a blood pressure; and said processor is configured to provide said condition signal based at least in part on said relationship.

15. The monitor of claim 1, wherein:

said processor is configured to determine a derivative of a propagation parameter of said received exciter waveform and to process said derivative to provide said condition signal.

16. The monitor of claim 15, wherein:

said processor is, configured to compare said condition signal to a previously stored condition signal provide a relative condition signal related to said physical condition.

17. The monitor of claim 1, wherein:

said physical condition is a mechanical property of said blood vessel; and said processor is configured to process said noninvasive sensor signal to provide said condition signal related to said mechanical property.

18. The monitor of claim 17, wherein:

said processor is configured to compare said condition signal to a previously stored condition signal provide a relative condition signal related to said physical condition.

19. A processor for use in determining a patient's physical condition with an apparatus having an exciter positioned over a blood vessel of the patient and configured to induce a transmitted exciter waveform into the patient, and a noninvasive sensor spaced apart from said exciter and adapted to be positioned over said blood vessel and configured to sense a hemoparameter and to generate a noninvasive sensor signal representative of said hemoparameter, said processor comprising:

a first input configured to receive said noninvasive sensor signal; and a determination routine configured to process said noninvasive sensor signal to determine a physical property of the patient in order to provide a condition signal related to said physical condition.

20. The processor of claim 19, wherein said apparatus includes a device configured to provide a pressure signal representative of a blood pressure of the patient, said processor further comprising:

a second input configured to receive said pressure signal; and an output pressure routine configured to provide said pressure signal as an output.

21. The processor of claim 20, further comprising:

a comparison routine configured to compare said condition signal to a previously stored condition signal to provide a relative condition signal related to said physical condition.

22. The processor of claim 19, wherein said apparatus includes a device configured to provide a pressure signal representative of a blood pressure of the patient, said processor further comprising:

a second input configured to receive said pressure signal; and wherein said determination routine is configured to process said pressure signal to provide said condition signal.

23. The processor of claim 22, further comprising:

a comparison routine configured to compare said condition signal to a previously stored condition signal to provide a relative condition signal related to said physical condition.

24. The processor of claim 22, further comprising:

a propagation routine configured to determine a propagation parameter of said received exciter waveform; and wherein said determination routine is configured to process said propagation parameter and said pressure signal to provide said condition signal.

25. The processor of claim 24, further comprising:

a relationship routine configured to determine a relationship between a propagation parameter and blood pressure; and wherein said determination routine is configured to provide said condition signal based at least in part on said relationship.

26. The processor of claim 22, further comprising:

a derivative routine configured to determine a derivative of a propagation parameter of said received exciter waveform; and wherein said determination routine is configured to process said derivative and said pressure signal to provide said condition signal.

27. The processor of claim 26, further comprising:

a comparison routine configured to compare said condition signal to a previously stored condition signal to provide a relative condition signal related to said physical condition.

28. The monitor of claim 22, wherein:

said physical condition is a mechanical property of said blood vessel; and said determination routine is configured to process said pressure signal to provide said condition signal related to said mechanical property.

29. The monitor of claim 28, further comprising:

a comparison routine configured to compare said condition signal to a previously stored condition signal to provide a relative condition signal related to said physical condition.

30. The processor of claim 19, further comprising:

a comparison routine configured to compare said condition signal to a previously stored condition signal to provide a relative condition signal related to said physical condition.

31. The processor of claim 19, further comprising:

a propagation routine configured to determine a propagation parameter of said received exciter waveform; and wherein said determination routine is configured to process said propagation parameter to provide said condition signal.

32. The processor of claim 19, further comprising:

a memory configured to store a relationship between a propagation parameter and blood pressure; and wherein said determination routine is configured to provide said condition signal based at least in part on said relationship.

33. The processor of claim 19, further comprising:

a derivative routine configured to determine a derivative of a propagation parameter of said received exciter waveform; and wherein said determination routine is configured to process said derivative to provide said condition signal.

34. The processor of claim 33, further comprising:

a comparison routine configured to compare said condition signal to a previously stored condition signal to provide a relative condition signal related to said physical condition.

35. The processor of claim 19, wherein:

said physical condition is a mechanical property of said blood vessel; and said determination routine is configured to provide said condition signal related to said mechanical property.

36. The monitor of claim 35, further comprising:

a comparison routine configured to compare said condition signal to a previously stored condition signal to provide a relative condition signal related to said physical condition.

37. A method for use in determining a patient's physical condition, comprising the steps of:

inducing a transmitted exciter waveform into the patient at a first location;

noninvasively sensing a hemoparameter at a location spaced apart from said first location and generating a noninvasive sensor signal representative of said hemoparameter containing a component of a received exciter waveform;

processing said noninvasive sensor signal to determine a physical property of the patient in order to provide a condition signal related to said physical condition.

38. The method of claim 37, further comprising the step of:

providing a calibration signal representative of the patient's physiological parameter and storing the calibration signal; and wherein said processing step includes a step of providing said pressure signal as an output.

39. The method of claim 38, further comprising the step of:

comparing said condition signal to a previously stored condition signal to provide a relative condition signal related to said physical condition.

40. The method of claim 37, further comprising the step of:

providing a calibration signal representative of the patient's physiological parameter and storing the calibration signal; and wherein said processing step is performed by processing said pressure signal to provide said condition signal.

41. The method of claim 40, further comprising the step of:

comparing said condition signal to a previously stored condition signal to provide a relative condition signal related to said physical condition.

42. The method of claim 39, further comprising the step of:

determining a propagation parameter of said received exciter waveform; and wherein said processing step is performed by processing said propagation parameter and said pressure signal to provide said condition signal.

43. The method of claim 42, further comprising the step of:

determining a relationship between said propagation parameter and said pressure signal; and wherein said processing step is performed to provide said condition signal based at least in part on said relationship.

44. The method of claim 39, further comprising the step of:

determining a derivative of a propagation parameter of said received exciter waveform; and wherein said processing step is performed by processing said derivative and said pressure signal to provide said condition signal.

45. The method of claim 44, further comprising the step of:

comparing said condition signal to a previously stored condition signal to provide a relative condition signal related to said physical condition.

46. The method of claim 39, wherein:

said physical condition is a mechanical property of said blood vessel; and said processing step is performed to process said noninvasive sensor signal and said pressure signal to provide said condition signal related to said mechanical property.

47. The method of claim 46, further comprising the step of:

comparing said condition signal to a previously stored condition signal to provide a relative condition signal related to said physical condition.

48. The method of claim 37, further comprising the step of:

comparing said condition signal to a previously stored condition signal to provide a relative condition signal related to said physical condition.

49. The method of claim 37, further comprising the step of:

determining a propagation parameter of said received exciter waveform; and wherein said processing step is performed by processing said propagation parameter to provide said condition signal.

50. The method of claim 37, further comprising the step of:

storing a relationship between a propagation parameter and a blood pressure; and wherein said processing step is performed to provide said condition signal based at least in part on said relationship.

51. The method of claim 37, further comprising the step of:

determining a derivative of a propagation parameter of said received exciter waveform; and wherein said processing step is performed by processing said derivative to provide said condition signal.

52. The method of claim 51, further comprising the step of:

comparing said condition signal to a previously stored condition signal to provide a relative condition signal related to said physical condition.

53. The method of claim 37, wherein:

said physical condition is a mechanical property of said blood vessel; and said processing step is performed to process said noninvasive sensor signal to provide said condition signal related to said mechanical property.

54. The method of claim 53, further comprising the step of:

comparing said condition signal to a previously stored condition signal to provide a relative condition signal related to said physical condition.

55. A monitor for use in determining a patient's physical condition, comprising:

a device configured to provide a pressure signal representative of a blood pressure of the patient;

an exciter adapted to be positioned over a blood vessel of the patient and configured to induce a transmitted exciter waveform into the patient;

a noninvasive sensor spaced apart from said exciter and adapted to be positioned over said blood vessel from said exciter and configured to sense a hemoparameter and to generate a noninvasive sensor signal representative of said hemoparameter containing a component of a received exciter waveform; and a processor coupled to said noninvasive sensor and configured to receive said noninvasive sensor signal and said pressure signal and to process said noninvasive sensor signal and said pressure signal to determine a physical property of the patient in order to provide a condition signal related to said physical condition.

56. The monitor of claim 55, wherein:

said processor is configured to determine a velocity of said transmitted exciter waveform and to process said velocity to provide said condition signal.

57. The monitor of claim 56, wherein:

said processor is configured to determine a relationship between the velocity of said transmitted exciter waveform and said pressure signal; and said processor is configured to provide said condition signal based at least in part on said relationship.

* * * * *